(12) United States Patent
Lee et al.

(10) Patent No.: US 11,515,500 B2
(45) Date of Patent: Nov. 29, 2022

(54) DISPLAY DEVICE

(71) Applicant: Samsung Display Co., Ltd., Yongin-si (KR)

(72) Inventors: Mi Hwa Lee, Seoul (KR); Su Jeong Kim, Yongin-si (KR); Yi Su Kim, Seoul (KR); Yi Seop Shim, Suwon-si (KR); Jin Hyeong Lee, Hwaseong-si (KR); Eun Jae Jeong, Hwaseong-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 236 days.

(21) Appl. No.: 16/907,752

(22) Filed: Jun. 22, 2020

(65) Prior Publication Data

US 2021/0143360 A1    May 13, 2021

(30) Foreign Application Priority Data

Nov. 12, 2019   (KR) .................. 10-2019-0144223

(51) Int. Cl.

| | | |
|---|---|---|
| *H01L 51/52* | (2006.01) | |
| *H01L 27/32* | (2006.01) | |
| *C07D 333/76* | (2006.01) | |
| *C07D 307/91* | (2006.01) | |
| *C07C 49/83* | (2006.01) | |
| *C07C 49/84* | (2006.01) | |
| *C07C 69/54* | (2006.01) | |
| *C07C 47/565* | (2006.01) | |

(52) U.S. Cl.
CPC ........ *H01L 51/5237* (2013.01); *C07C 47/565* (2013.01); *C07C 49/83* (2013.01); *C07C 49/84* (2013.01); *C07C 69/54* (2013.01); *C07D 307/91* (2013.01); *C07D 333/76* (2013.01); *H01L 27/322* (2013.01); *H01L 27/323* (2013.01); *H01L 51/5284* (2013.01); *C07C 2602/26* (2017.05); *C07C 2603/24* (2017.05); *C07C 2603/48* (2017.05); *C07C 2603/50* (2017.05)

(58) Field of Classification Search
None
See application file for complete search history.

(56) References Cited

FOREIGN PATENT DOCUMENTS

| KR | 10-1521775 B1 | 5/2015 |
|---|---|---|
| KR | 10-2017-0050742 A | 5/2017 |
| KR | 10-2019-0009875 A | 1/2019 |
| KR | 10-2019-0012305 A | 2/2019 |
| KR | 10-2019-0025283 A | 3/2019 |
| KR | 10-2019-0058405 A | 5/2019 |

OTHER PUBLICATIONS

Machine English translation of Han et al. (KR 10-2019-0058405). Apr. 11, 2022.*

* cited by examiner

*Primary Examiner* — Jay Yang
(74) *Attorney, Agent, or Firm* — Lewis Roca Rothgerber Christie LLP

(57) ABSTRACT

A display device includes: a base substrate; a light emitting element on the base substrate; a thin film encapsulation layer on the light emitting element to encapsulate the light emitting element; a touch member on the thin film encapsulation layer; a color filter layer on the touch member; and a planarization layer on the color filter layer to cover the color filter layer, wherein the planarization layer includes a light absorber represented by Formula 1:

X—Ar—Y.                                                                  Formula 1

20 Claims, 21 Drawing Sheets

FIG. 5
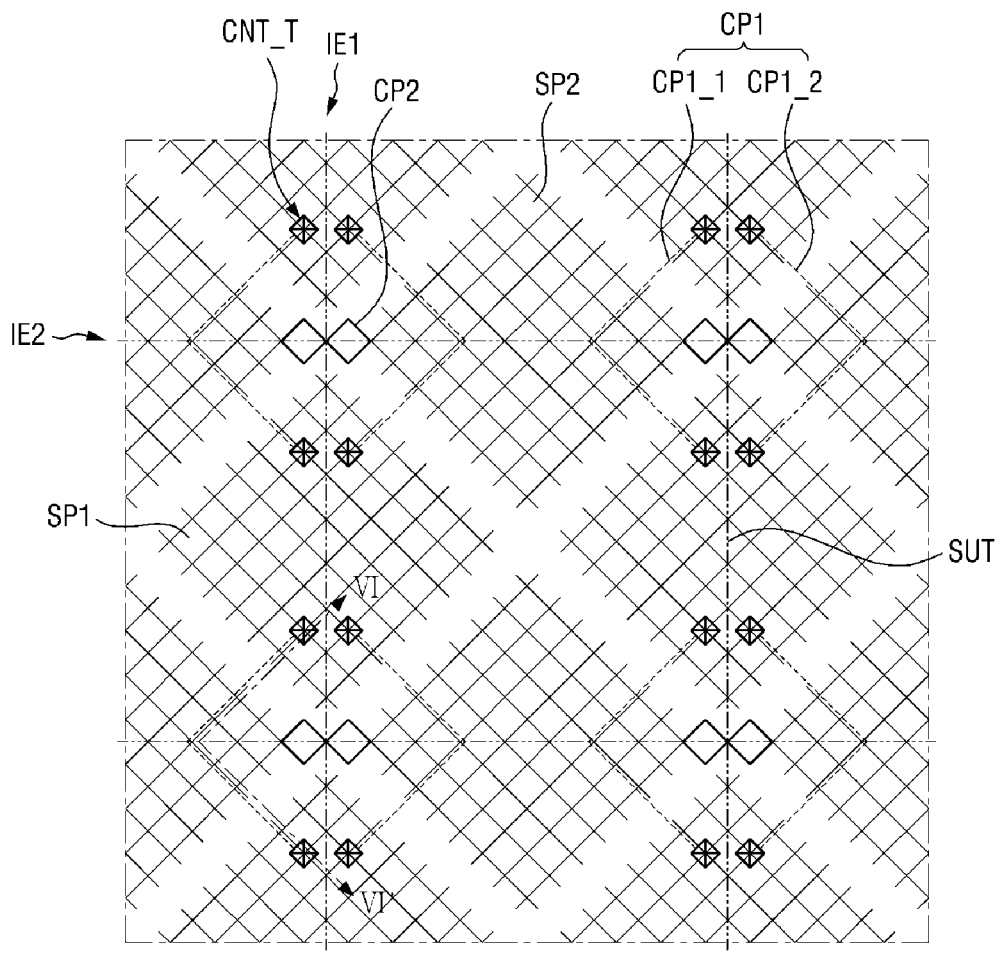
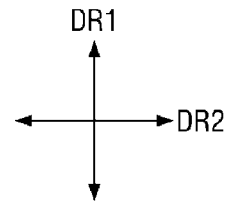

DISPLAY DEVICE

CROSS-REFERENCE TO RELATED APPLICATION

This application claims priority to and the benefit of Korean Patent Application No. 10-2019-0144223 filed on Nov. 12, 2019 in the Korean Intellectual Property Office, the entire content of which is incorporated herein by reference.

BACKGROUND

1. Field

One or more aspects of embodiments of the present disclosure relate to a display device.

2. Description of the Related Art

A display device for displaying an image may be used for various electronic appliances for providing an image to a user, such as smart phones, tablet PCs, digital cameras, notebook computers, navigators, and/or televisions. A display device includes a display panel for generating and displaying an image, and various input devices. An example display device may include a light emitting element having a light emitting layer to display an image on a screen to a user.

However, as outdoor use of display devices increases, a light emitting layer included in a light emitting element may be damaged by external ultraviolet light. Due to the damage of the light emitting layer, luminance may decrease, and light emitting area itself may decrease, thereby causing the deterioration of element characteristics.

SUMMARY

One or more aspects of embodiments of the present disclosure are directed toward a display device capable of preventing or reducing the deterioration of characteristics of a light emitting element.

According to an embodiment, a display device includes a base substrate, a light emitting element on the base substrate, a thin film encapsulation layer on the light emitting element to encapsulate the light emitting element, a touch member on the thin film encapsulation layer, a color filter layer on the touch member, and a planarization layer on the color filter layer to cover the color filter layer, wherein the planarization layer includes a light absorber represented by Formula 1:

X—Ar—Y,  Formula 1 wherein, in Formula 1, Ar may be pyrene, chrysene, or anthracene, Y may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or may be represented by any one of Structural Formulae below:

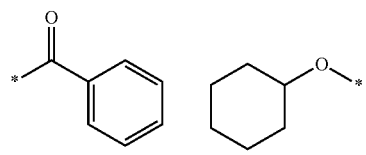

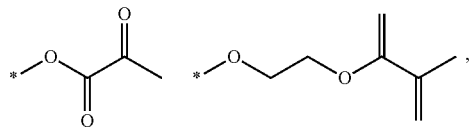

and

X may be represented by any one of Formulae 2-1 to 2-3:

Formula 2-1

Formula 2-2

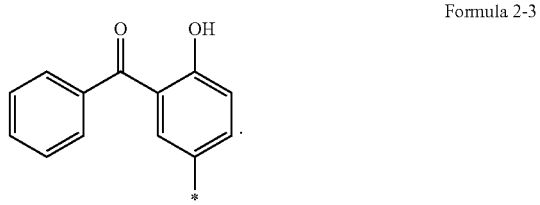

Formula 2-3

Formula 1 may be represented by any one of Formulae 1-1 to 1-3:

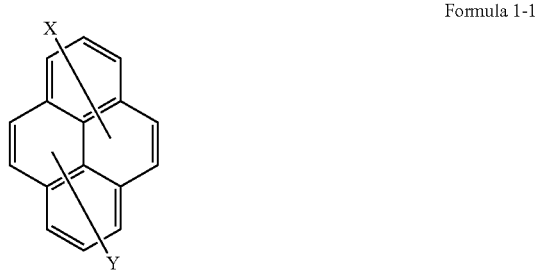

Formula 1-1

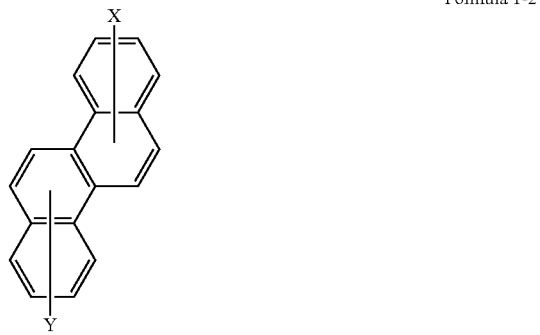

Formula 1-2

Formula 1-3

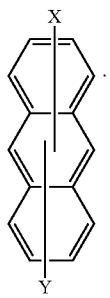

Formula 1 may be represented by any one of Formulae 1-4 to 1-6:

Formula 1-4

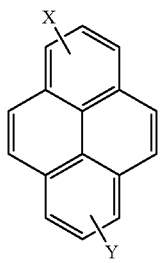

Formula 1-5

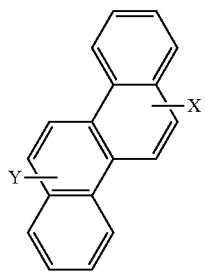

Formula 1-6

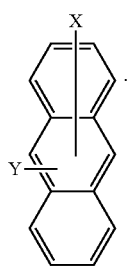

Formula 1 may be represented by any one of Formulae 1-7 to 1-9:

Formula 1-7

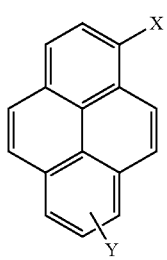

Formula 1-8

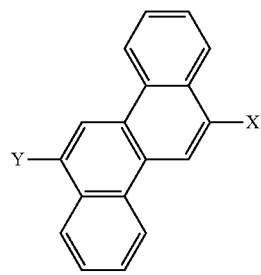

Formula 1-9

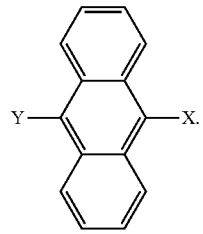

X may be represented by Formula 2-1, and Y may be represented by Formula 3:

Formula 3

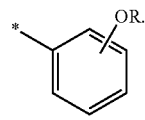

The display device may have an absorbance of 0.7 or more in a wavelength band of 380 nm to 410 nm.

The light absorber represented by Formula 1 may be any one selected from compounds represented by Compound Group 1:

Compound Group 1

1

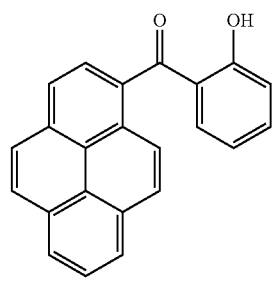

2

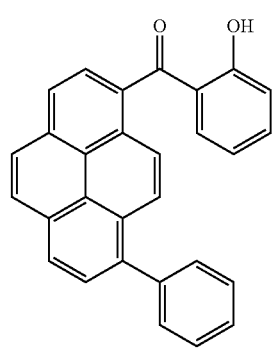

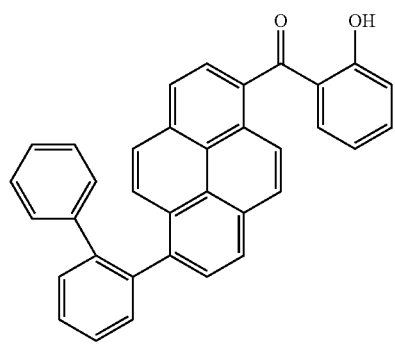
3
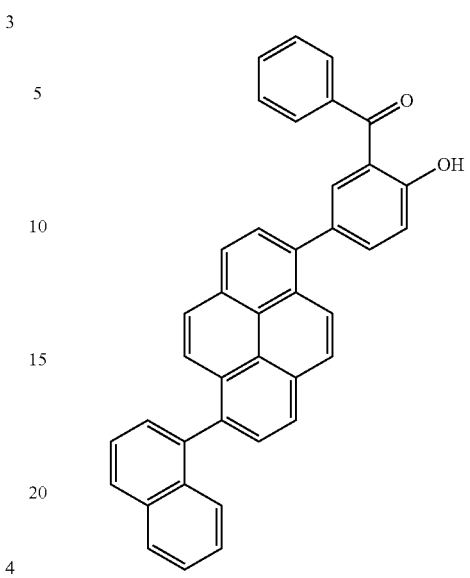
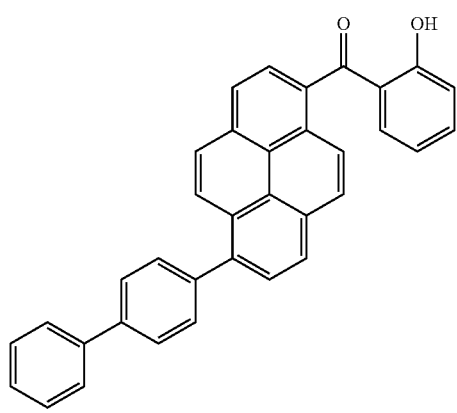
4
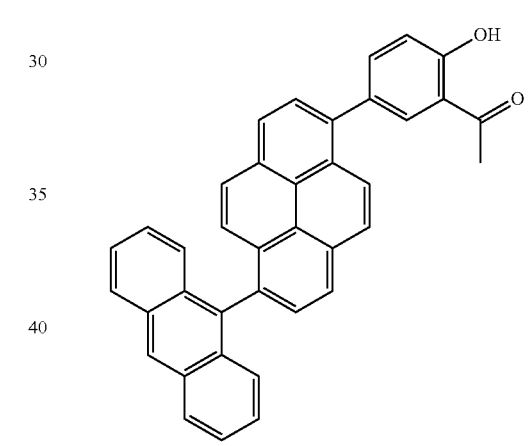
5
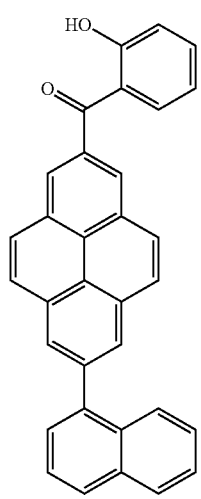
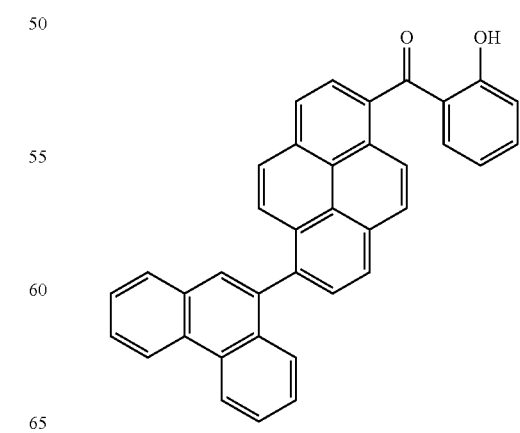

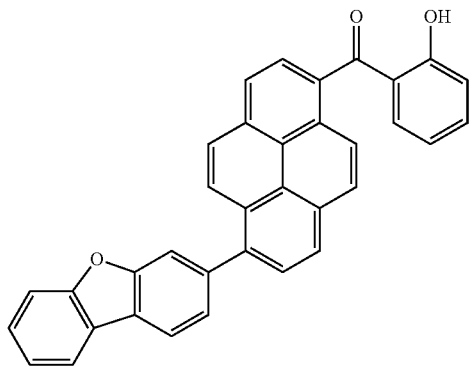
9
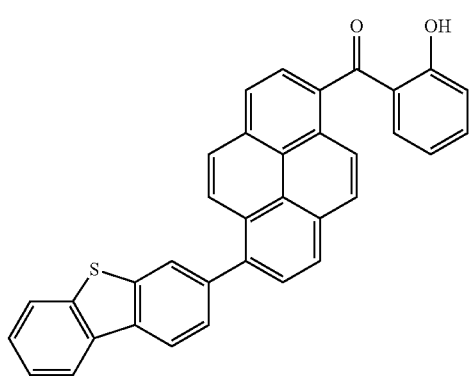
13
10
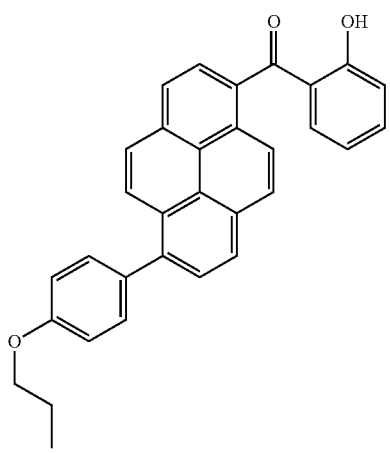
14
11
12
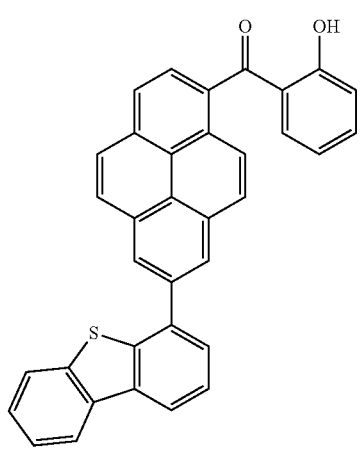
15

16
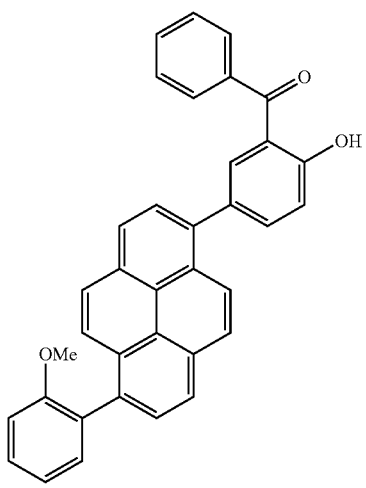
17
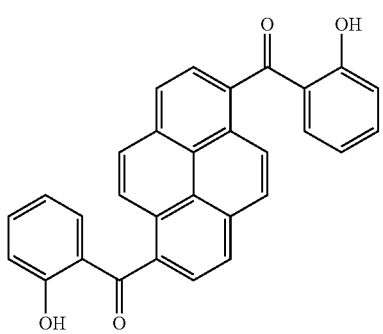
18
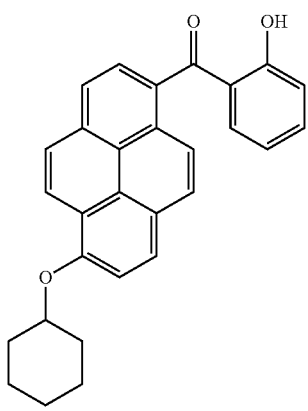
19
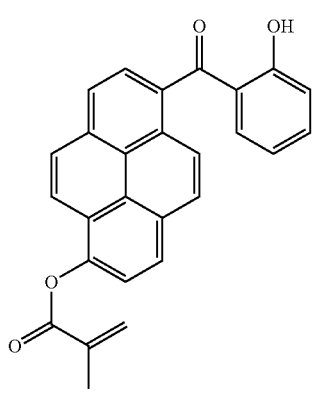
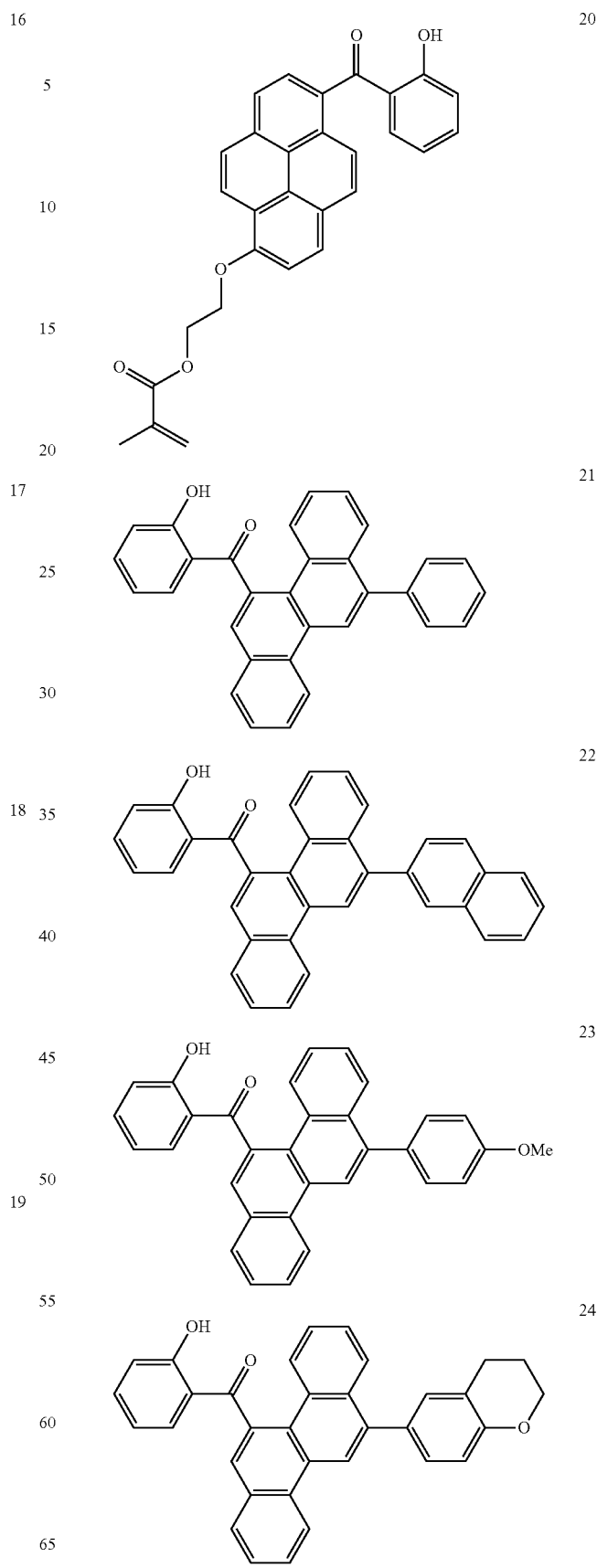

25
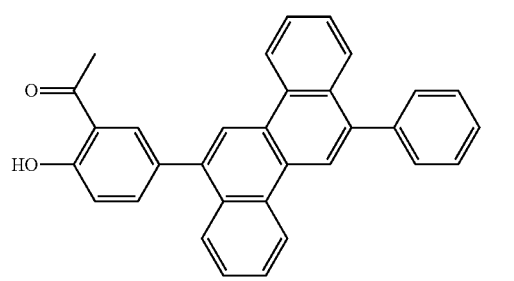
26
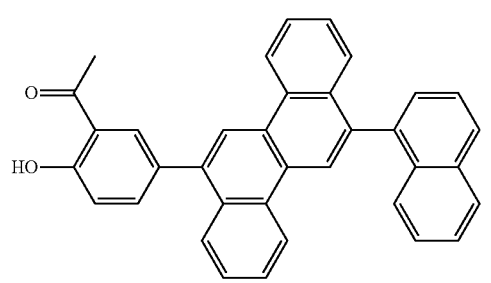
27
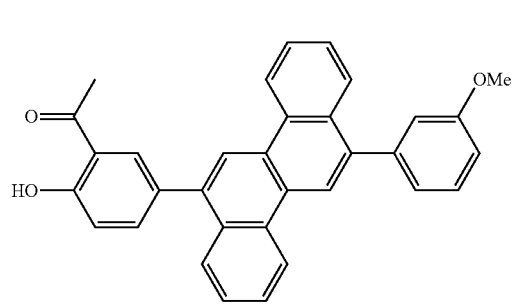
28
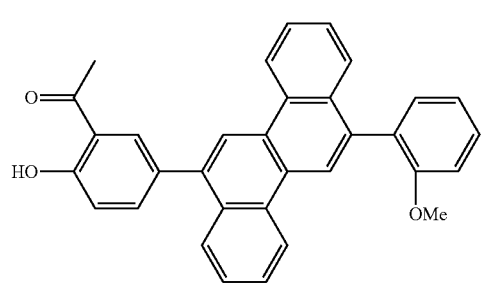
29
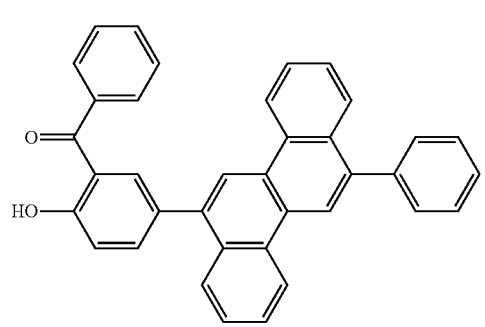
30
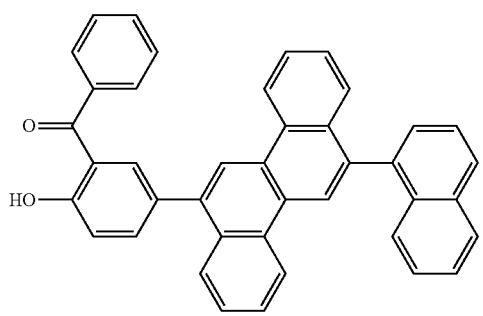
31
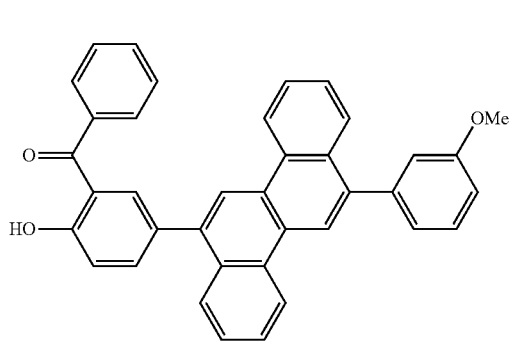
32
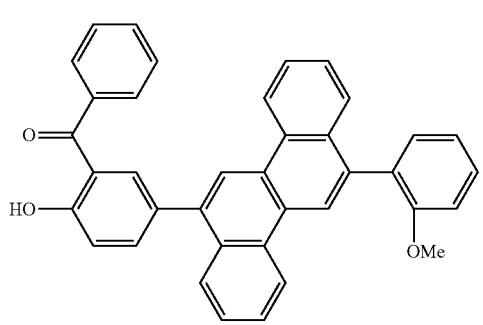
33
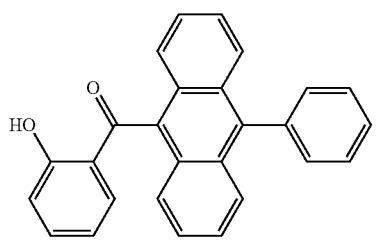
34
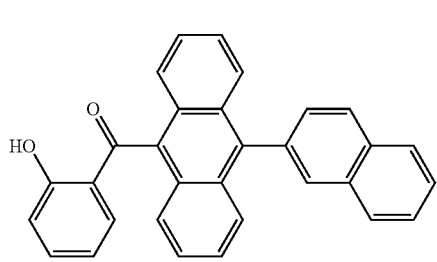

-continued

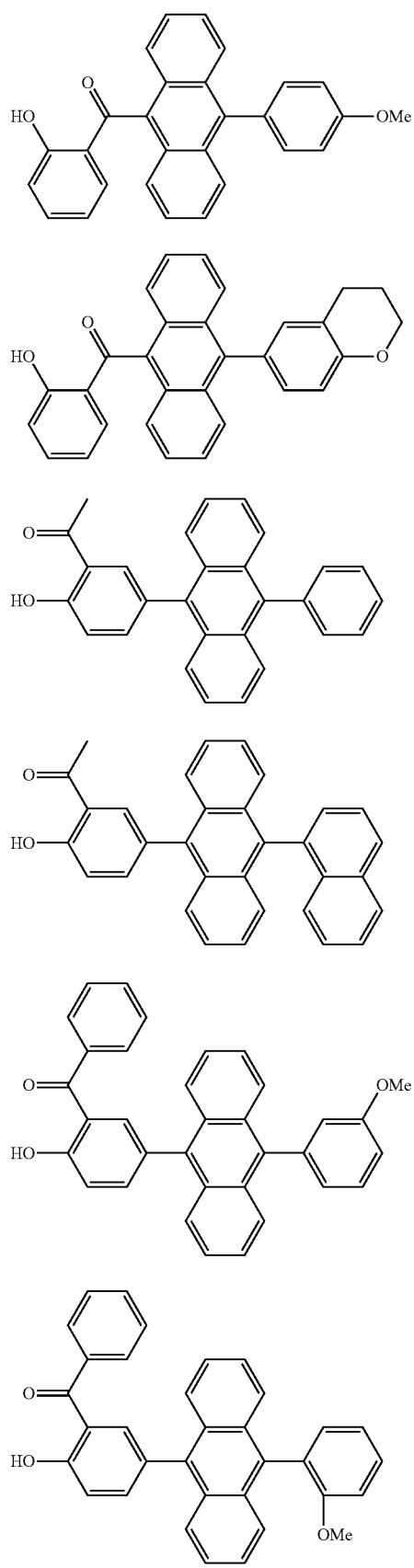

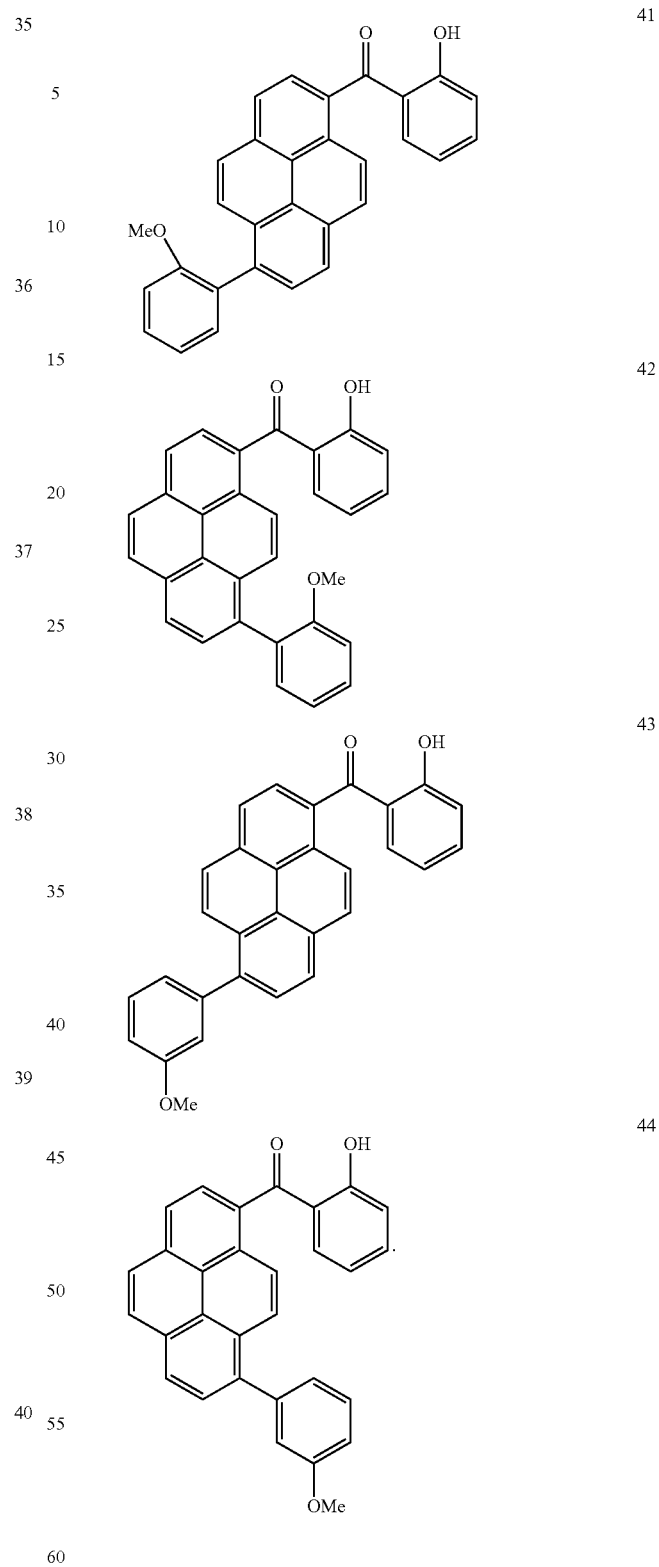

The light absorber may be in the color filter layer.

The color filter layer may be provided for each pixel, the color filter layer may include a plurality of color filters and the plurality of color filters may be spaced apart from each other at a boundary between adjacent pixels, and a light blocking layer may be on the touch member at the boundary between adjacent pixels.

The touch member may include a first touch conductive layer, a first touch insulating layer on the first touch conductive layer, a second touch conductive layer on the first touch insulating layer, and a second touch insulating layer on the second touch conductive layer; and the light absorber may be further provided in the first touch insulating layer and/or the second touch insulating layer.

The first touch conductive layer may be directly on the thin film encapsulation layer.

According to another embodiment, a display device includes a base substrate, a light emitting element on the base substrate, a thin film encapsulation layer on the light emitting element to encapsulate the light emitting element, a touch member on the thin film encapsulation layer, a color filter layer on the touch member, and a planarization layer on the color filter layer to cover the color filter layer, wherein the planarization layer includes a light absorber in a content of 3% to 25%.

The light absorber may be represented by Formula 1:

$$X—Ar—Y, \quad \text{Formula 1}$$

In Formula 1, Ar may be pyrene, chrysene, or anthracene, Y may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or may be represented by any one of Structural Formulae:

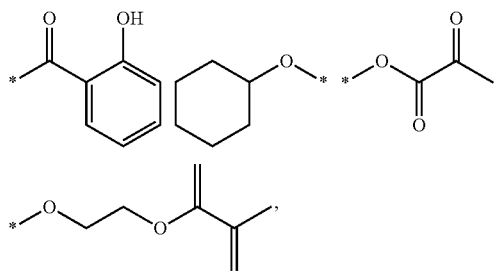

and

X may be represented by any one of Formulae 2-1 to 2-3:

Formula 2-1

Formula 2-2

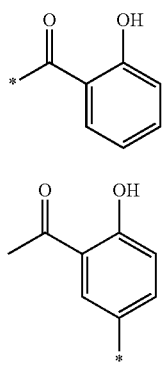

Formula 2-3

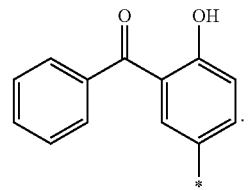

The light absorber may be further provided in the color filter layer.

The color filter layer may be provided for each pixel, the color filter layer may include a plurality of color filters and the plurality of color filters may be spaced apart from each other at a boundary between adjacent pixels, and a light blocking layer may be on the touch member at the boundary between adjacent pixels.

The touch member may include a first touch conductive layer, a first touch insulating layer on the first touch conductive layer, a second touch conductive layer on the first touch insulating layer, and a second touch insulating layer on the second touch conductive layer; and the light absorber may be further provided in the first touch insulating layer and/or the second touch insulating layer.

According to still another embodiment, a display device includes a base substrate, a light emitting element on the base substrate, a thin film encapsulation layer on the light emitting element to encapsulate the light emitting element, a touch member on the thin film encapsulation layer, and an optical member on the touch member, wherein the touch member includes a first touch conductive layer, a first touch insulating layer on the first touch conductive layer, a second touch conductive layer on the first touch insulating layer, and a second touch insulating layer on the second touch conductive layer, a light absorber is provided in the first touch insulating layer and/or the second touch insulating layer, and the light absorber is represented by Formula 1:

$$X—Ar—Y, \quad \text{Formula 1}$$

In Formula 1, Ar may be pyrene, chrysene, or anthracene, Y may be a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or may be represented by any one of Structural Formulae:

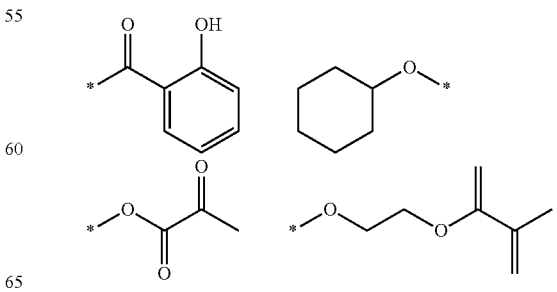

and
X may be represented by any one of Formulae 2-1 to 2-3:
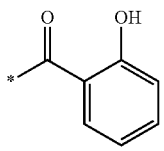
Formula 2-1
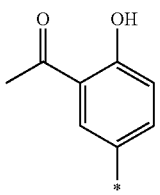
Formula 2-2
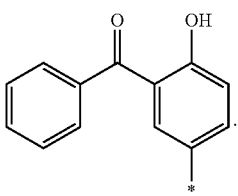
Formula 2-3
Formula 1 may be represented by any one of Formulae 1-1 to 1-3:
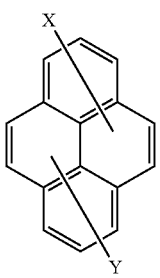
Formula 1-1
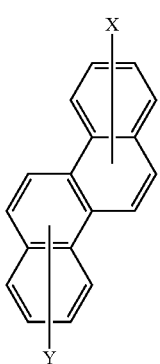
Formula 1-2
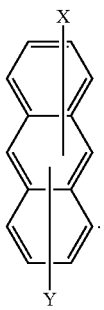
Formula 1-3
Formula 1 may be represented by any one of Formulae 1-4 to 1-6:
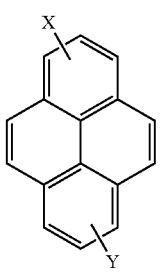
Formula 1-4
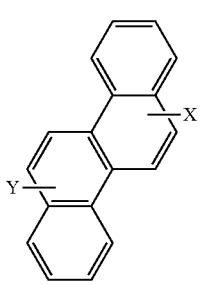
Formula 1-5
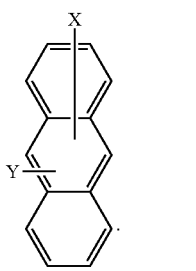
Formula 1-6
Formula 1 may be represented by any one of Formulae 1-7 to 1-9:
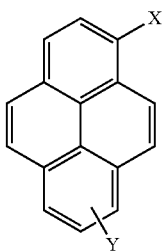
Formula 1-7

Formula 1-8

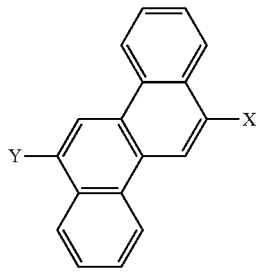

Formula 1-9

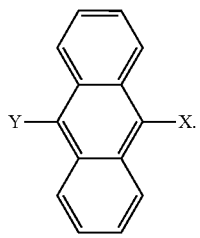

However, aspects of the present disclosure are not restricted to those set forth herein. The above and other aspects of the present disclosure will become more apparent to one of ordinary skill in the art to which the present disclosure pertains by referencing the detailed description of the present disclosure.

BRIEF DESCRIPTION OF THE DRAWINGS

The above and other aspects and features of the present disclosure will become more apparent by describing in more detail example embodiments thereof with reference to the attached drawings, in which:

FIG. 5 is a partially enlarged view of the touch area of FIG. 4;

DETAILED DESCRIPTION

Figure 1:
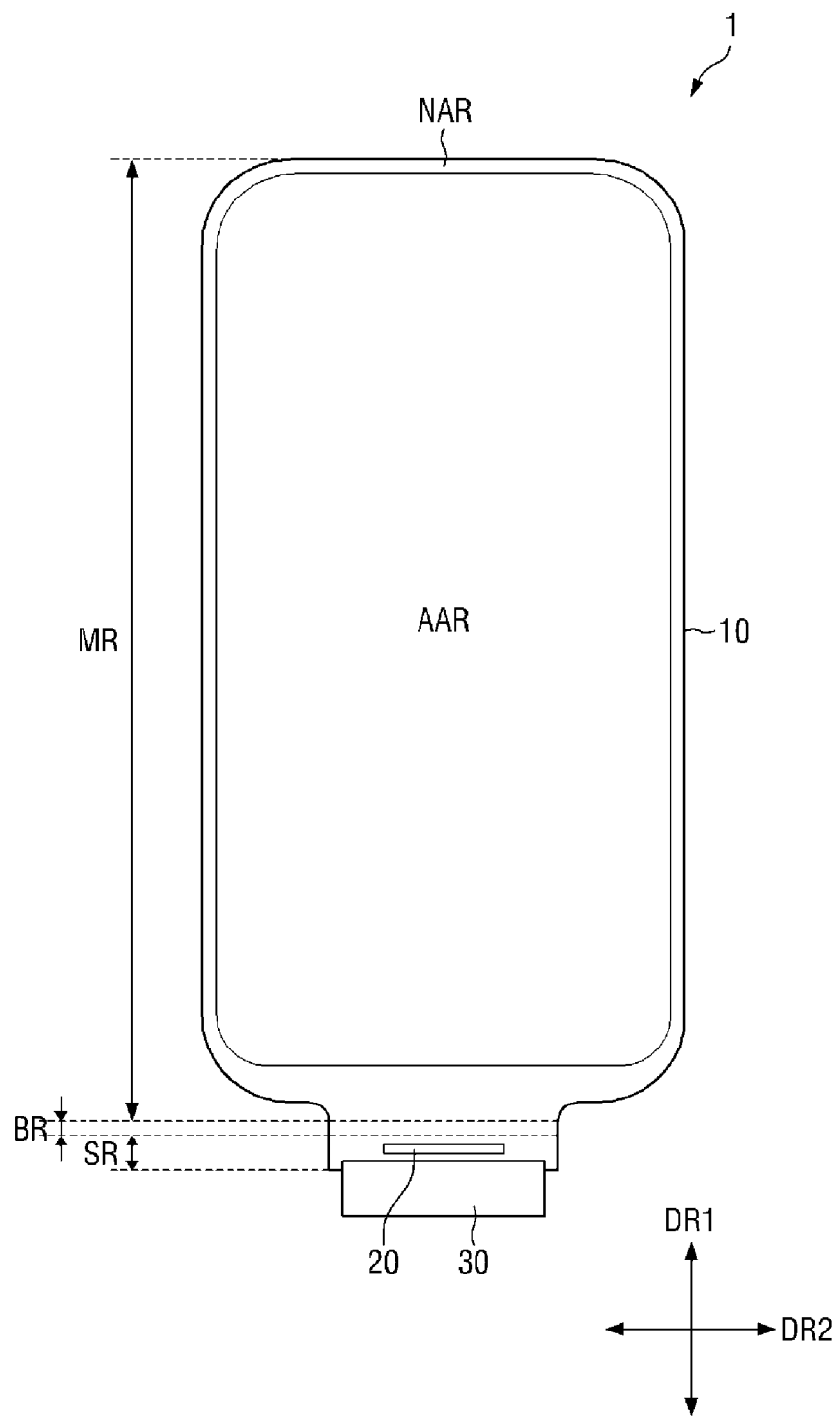
FIG. 1 is a plan layout view of a display device according to an embodiment.

The advantages and features of the present disclosure and methods for achieving the advantages and features will be apparent by referring to the embodiments to be described herein in more detail with reference to the accompanying drawings. However, the present disclosure is not limited to the embodiments disclosed hereinafter, but can be implemented in diverse forms. The matters defined in the description, such as the detailed construction and elements, are details provided to assist those of ordinary skill in the art in a comprehensive understanding of the present disclosure, and the present disclosure is only defined within the scope of the appended claims.

Where an element is described as being related to another element, such as being "on" or "located on," another element or layer, both a case where an element is located directly on another element or a layer (without any intervening element(s) therebetween) and a case where an element is located on another element via another layer or another element are included. Like reference numerals refer to like elements throughout the specification.

Although the terms "first," "second," and the like are used to describe various components, these components may not be limited by these terms. These terms are only used to distinguish one component from another component. Therefore, the first component may also be a second component within the technical spirit of the present disclosure.

The term "and/or" includes one or more combinations which may be defined by relevant elements. Expressions such as "at least one of," "one of," and "selected from," when preceding a list of elements, modify the entire list of elements and do not modify the individual elements of the list. Further, the use of "may" when describing embodiments of the present disclosure refers to "one or more embodiments of the present disclosure."

Hereinafter, embodiments of the present disclosure will be described with reference to the attached drawings.

Figure 2:
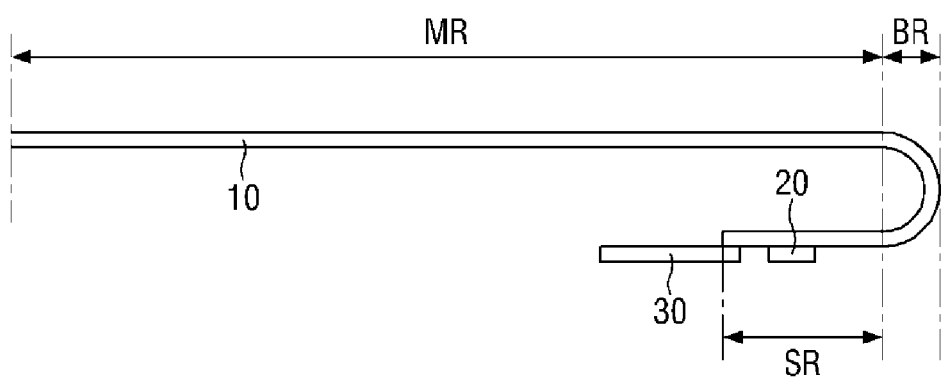
FIG. 2 is a schematic partial cross-sectional view of a display device according to an embodiment.

FIG. 1 is a plan layout view of a display device according to an embodiment, and FIG. 2 is a schematic partial cross-sectional view of a display device according to an embodiment.

In embodiments, a first direction DR1 and a second direction DR2 cross (or intersect) each other in different directions. In the plan view of FIG. 1, for convenience of description, the first direction DR1, which is a vertical direction, and the second direction DR2, which is a horizontal direction, are defined. In the following embodiments, one side (e.g., one half) of the first direction DR1 axis refers to an upward direction in the plan view, the other side (e.g., the other half) of the first direction DR1 axis refers to a downward direction in the plan view, one side (e.g., one half) of the second direction DR2 axis refers to a right direction in the plan view, and the other side (e.g., the other half) of the second direction DR2 axis refers to a left direction in the plan view. However, the directions mentioned in the embodiments should be understood to refer to relative directions, and the embodiments are not limited to the aforementioned directions.

Referring to FIGS. 1 and 2, a display device 1 may refer to any electronic device that can provide a display of images. Examples of the display device 10 may include various suitable products such as televisions, notebooks, monitors, billboards, and/or internet of things items, as well as portable electronic appliances such as mobile phones, smart phones, tablet personal computers (PCs), smart watches, watch phones, mobile communication terminals, electronic notebooks, electronic books, portable multimedia players (PMPs), navigators, and/or ultra mobile PCS (UMPs).

The display device 1 includes an active area AAR and a non-active area NAR. In the display device 1, when a portion displaying a screen (e.g., an image) is defined as a display area, a portion not displaying the screen is defined as a non-display area, and an area where a touch input is detected is defined as a touch area. The display area and the touch area may be included in the active area AAR. The display area and the touch area may overlap each other. For example, the active area AAR may be an area where display is performed and touch input is also detected. The shape of the active area AAR may be a rectangle or a rectangle having rounded corners, but is not limited thereto. For example, the shape of the active area AAR may be a rectangle, which has rounded corners and which is longer in the first direction DR1 than in the second direction DR2. However, the present disclosure is not limited thereto, and the active area AAR may have various suitable shapes such as a rectangle which is longer in the second direction DR2 than in the first direction DR1, a square, other polygons, a circle, and/or an ellipse.

The non-active area NAR may be around the active area AAR. The non-active area NAR may be a bezel area. The non-active area NAR may surround all sides (e.g., four sides as shown in the drawings) of the active area AAR. However, the present disclosure is not limited thereto. For example, the non-active area NAR may not be around the upper side of the active area AAR or around the left and/or right sides of the active area AAR.

Signal lines and/or driving circuits for applying signals to the active area AAR (display area and/or touch area) may be arranged in the non-active area NAR. The non-active area NAR may not include a display area. In some embodiments, the non-active area NAR may not include a touch area. In other embodiments, the non-active area NAR may include a part of the touch area, and a sensing member (such as a pressure sensor) may be provided in the corresponding area. In some embodiments, the active area AAR may be exactly the same area as the display area where a screen (e.g., an image) is displayed, and the non-active area NAR may be the same area as the non-display area where a screen (e.g., an image) is not displayed.

The display device 1 includes a display panel 10 that provides a display screen. Examples of the display panel may include an organic light emitting display panel, a micro LED display panel, a nano LED display panel, a quantum dot light emitting display panel, a liquid crystal display panel, a plasma display panel, a field emission display panel, an electrophoretic display panel, and an electrowetting display panel. Hereinafter, a case where the organic light emitting display panel is applied is illustrated as an example of the display panel 10. However, the present disclosure is not limited thereto, and the same technical idea may be applied to other suitable display panels.

The display panel 10 may include a plurality of pixels. The plurality of pixels may be arranged in a matrix direction (e.g., matrix formation). The shape of each pixel may be a rectangle or a square in a plan view, but is not limited thereto, and each pixel may have a rhombus shape in which each side is inclined with respect to the first direction DR1. Each pixel may include a light emitting area. Each light emitting area may have the same shape as the pixel, but may have a different shape from the pixel. For example, when the pixel has a rectangular shape, the light emitting area of the corresponding pixel may have various suitable shapes such as a rectangle, a rhombus, a hexagon, an octagon, and a circle. More details of each pixel and each light emitting area will be described later.

The display device 1 may further include a touch member that detects a touch input. The touch member may be provided as a panel or a film, separate from the display panel 10 and attached to the display panel 10, but may also be provided in the form of a touch layer inside the display panel 10. In the following embodiments, there is exemplified a case where the touch member is provided inside the display panel to be included in the display panel 10, but the present disclosure is not limited thereto.

The display panel 10 may include a flexible substrate including a flexible polymer material such as polyimide. Accordingly, the display panel 10 may be bent, warped, folded, and/or rolled.

The display panel 10 may include a bending area BR in which the panel is bent. The display panel 10 may be divided into a main area MR located at one side of the bending area BR and a sub-area SR located at the other side of the bending area BR (opposite from the main area MR), relative to the bending area BR.

The display area of the display panel 10 may be in the main area MR. In an embodiment, in the main area MR, edges around the display area, the entire bending area BR, and the entire sub-area SR may be non-display areas. However, the present disclosure is not limited thereto, and the bending area BR and/or the sub-area SR may include a display area.

The main area MR may have a shape similar to the planar appearance of the display device 1. For example, the main area MR may be a flat area located in one plane. However, the present disclosure is not limited thereto, and at least one of the remaining edges other than the edge (side) connected to the bending area BR may be curved in the main area MR, to form a curved surface, and/or may be bent in (along) the vertical direction. When at least one of the remaining edges of the main area MR, other than the edge (side) connected to the bending area BR, may be curved and/or bent, the display area may also be provided at the corresponding edge. However, the present disclosure is not limited thereto, and the curved and/or bent edge may be a non-display area that does not display the screen, or the display area and the non-display area may be mixed in the corresponding portion.

The bending area BR may be connected to one side of the main area MR in the first direction DR1. For example, the bending area BR may be connected through (e.g., to) the lower short side of the main area MR. The width (in the second direction DR2) of the bending area BR may be smaller than the width (short width, in the second direction DR2) of the main area MR. The connection portion of the main area MR and the bending area BR may have an L-shaped cutting shape.

In the bending area BR, the display panel 10 may be bent by being curved in a downward direction (in the thickness direction), that is, away from a display surface. The bending area BR may have a constant radius of curvature, but is not limited thereto, and may have a different radius of curvature for each section. As the display panel 10 is bent in the bending area BR, the surface of the display panel 10 may be reversed. For example, one surface of the display panel 10 (e.g., a portion of the surface of the display panel 10) initially facing upward may be changed (through bending) to first face outward through the bending area BR, and then face downward.

The sub-area SR extends from the bending area BR. The sub-area SR may extend in a direction parallel to the main area MR immediately after the bending is completed. When bent, the sub-area SR may overlap the main area MR in the thickness direction of the display panel 10. The width (width in the second direction DR2) of the sub-area SR may be equal to the width of the bending area BR, but the present disclosure is not limited thereto.

A driving chip IC may be provided in the sub-area SR. The driving chip IC may include an integrated circuit for driving the display panel 10. The integrated circuit may include an integrated circuit for a display and/or an integrated circuit for a touch unit. The integrated circuit for a display and the integrated circuit for a touch unit may be provided as separate chips or may be integrated into one chip.

A pad unit may be provided at an end of the sub-area SR of the display panel 10. The pad unit may include a plurality of display signal line pads and a plurality of touch signal line pads. A driving substrate FPC may be connected to the pad unit provided at the end of the sub-area SR of the display panel 10. The driving substrate FPC may be a flexible printed circuit board or a film.

Figure 3:
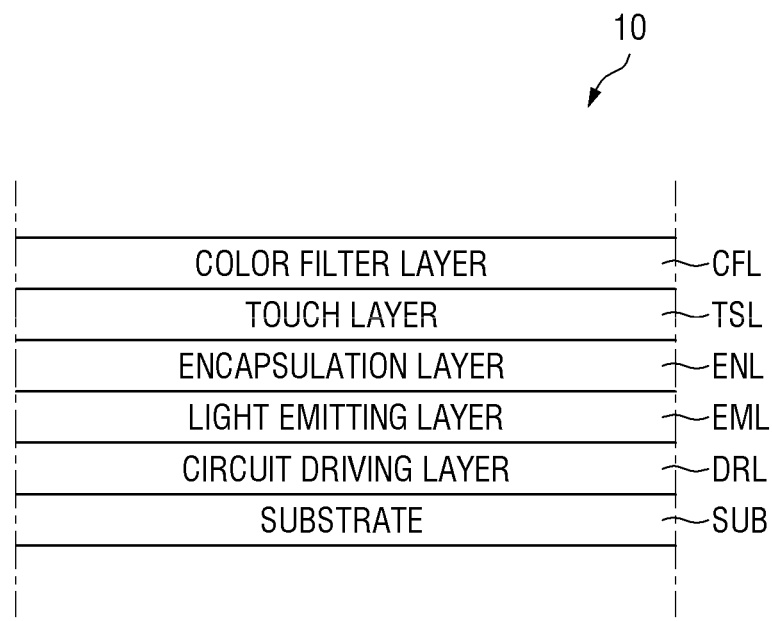
FIG. 3 is a schematic cross-sectional view illustrating an example laminate structure of a display panel according to an embodiment.

FIG. 3 is a schematic cross-sectional view illustrating an example laminate structure of a display panel according to an embodiment.

Referring to FIG. 3, the display panel 10 may include a circuit driving layer DRL on a substrate SUB. The circuit driving layer DRL may include a circuit for driving a light emitting layer 175 of a pixel. The circuit driving layer DRL may include a plurality of thin film transistors.

A light emitting layer 175 may be on the circuit driving layer DRL. The light emitting layer 175 may include an organic light emitting layer. The light emitting layer 175 may emit light of various luminance, according to a driving signal transmitted from the circuit driving layer DRL.

An encapsulation layer ENL may be on the light emitting layer 175. The encapsulation layer ENL may include an inorganic film or a laminated film of an inorganic film and an organic film. In some embodiments, a glass or an encapsulation film may be applied as the encapsulation layer ENL.

A touch layer TSL may be on the encapsulation layer ENL. The touch layer TSL is a layer that recognizes a touch input, and may function as a touch member. The touch layer TSL may include a plurality of sensing areas and a plurality of sensing electrodes.

A color filter layer CFL may be on the touch layer TSL. The color filter layer CFL may include a red color filter to transmit light of a red wavelength band and absorb and block (or substantially absorb and block) light of other wavelength bands, a green color filter to transmit light of a green wavelength band and absorb and block (or substantially absorb and block) light of other wavelength bands, and a blue color filter to transmit light of a blue wavelength band and absorb and block (or substantially absorb and block) light of other wavelength bands. The color filter layer CFL may not only improve color purity, but also reduce external light reflection in some cases.

Figure 4:
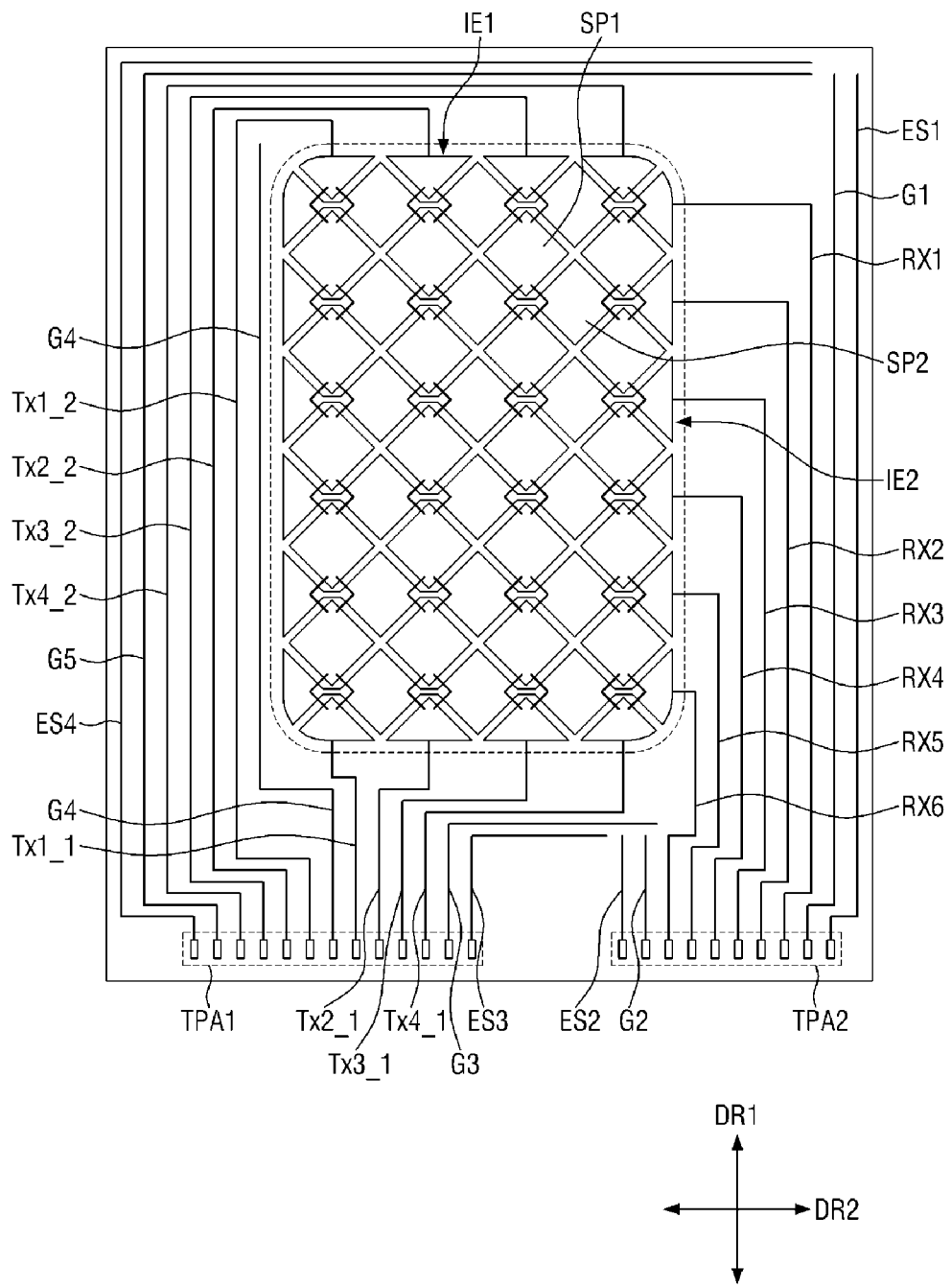
FIG. 4 is a schematic plan layout view of a touch member according to an embodiment.
Figure 6:
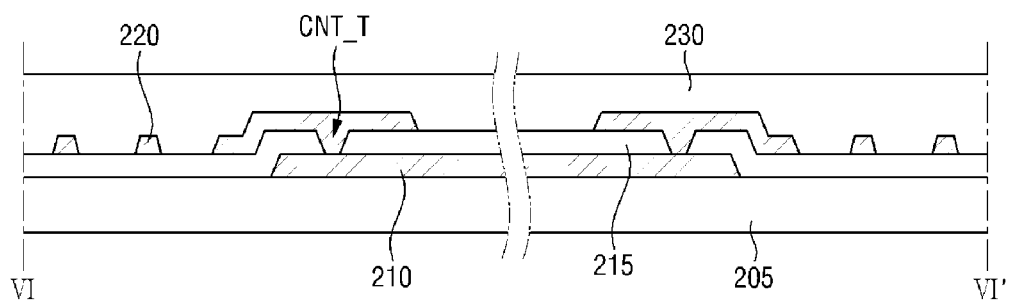
FIG. 6 is a cross-sectional view taken along line VI-VI' of FIG. 5.

FIG. 4 is a schematic plan layout view of a touch member according to an embodiment, FIG. 5 is a partially enlarged view of the touch area of FIG. 4, and FIG. 6 is a cross-sectional view taken along the line VI-VI' of FIG. 5.

Referring to FIGS. 4 to 6, the touch member may include a touch area located in the active area AAR and a non-touch area located in the non-active area NAR. For convenience of explanation, it is shown in FIG. 4 that the overall shape of the touch member is simplified and the non-touch area is relatively wide. However, in some embodiments, the shape of the touch area and the shape of the non-touch area may be substantially the same as the shape of the active area AAR and the shape of the non-active area NAR, respectively.

The touch area of the touch member may include a plurality of first sensing electrodes IE1 (or first touch electrodes) and a plurality of second sensing electrodes IE2 (or second touch electrodes). One of the first sensing electrode IE1 and the second sensing electrode IE2 may be a driving electrode, and the other thereof may be a sensing electrode. In the present example embodiment, there is exemplified a case where the first sensing electrode IE1 is a driving electrode and the second sensing electrode IE2 is a sensing electrode.

The first sensing electrode IE1 may extend in the first direction DR1. The first sensing electrode IE1 may include a plurality of first sensor portions SP1 arranged along the first direction DR1, and a first connection portion CP1 electrically connecting the first sensing electrode IE1 to the adjacent first sensor portion(s) SP1.

The plurality of first sensing electrodes IE1 may be arranged in the second direction DR2.

The second sensing electrode IE2 may extend in the second direction DR2.

The second sensing electrode IE2 may include a plurality of second sensor portions SP2 arranged along the second direction DR2 and a second connection portion CP2 electrically connecting the second sensing electrode IE2 to the adjacent second sensor portion(s) SP2. The plurality of second sensing electrodes IE2 may be arranged in the first direction DR1.

Although it is shown in the drawings that four first sensing electrodes IE1 and six second sensing electrodes IE2 are arranged, the number of the first sensing electrodes IE1 and the number of the second sensing electrodes IE2 are not limited thereto.

At least some of the first sensor portions SP1 and the second sensor portions SP2 may have a rhombus shape. Some of the first sensor portions SP1 and the second sensor portions SP2 may have a graphic shape cut from a rhombus shape. For example, all of the first sensor portions SP1 and the second sensor portions SP2 except for those located at both ends in the extension direction may have a rhombus shape, and the first sensor portions SP1 and the second sensor portions SP2 located at both ends in the extension direction may have a triangular shape in which a rhombus is cut in half. The rhombic first sensor portions SP1 and the rhombic second sensor portions SP2 may have substantially the same size and shape as each other. The triangular first sensor portions SP1 and the triangular second sensor portions SP2 may have substantially the same size and shape as each other. However, embodiments are not limited to that illustrated above, and the shapes and sizes of the first sensor portions SP1 and the second sensor portions SP2 may be variously suitably modified.

Figure 7:
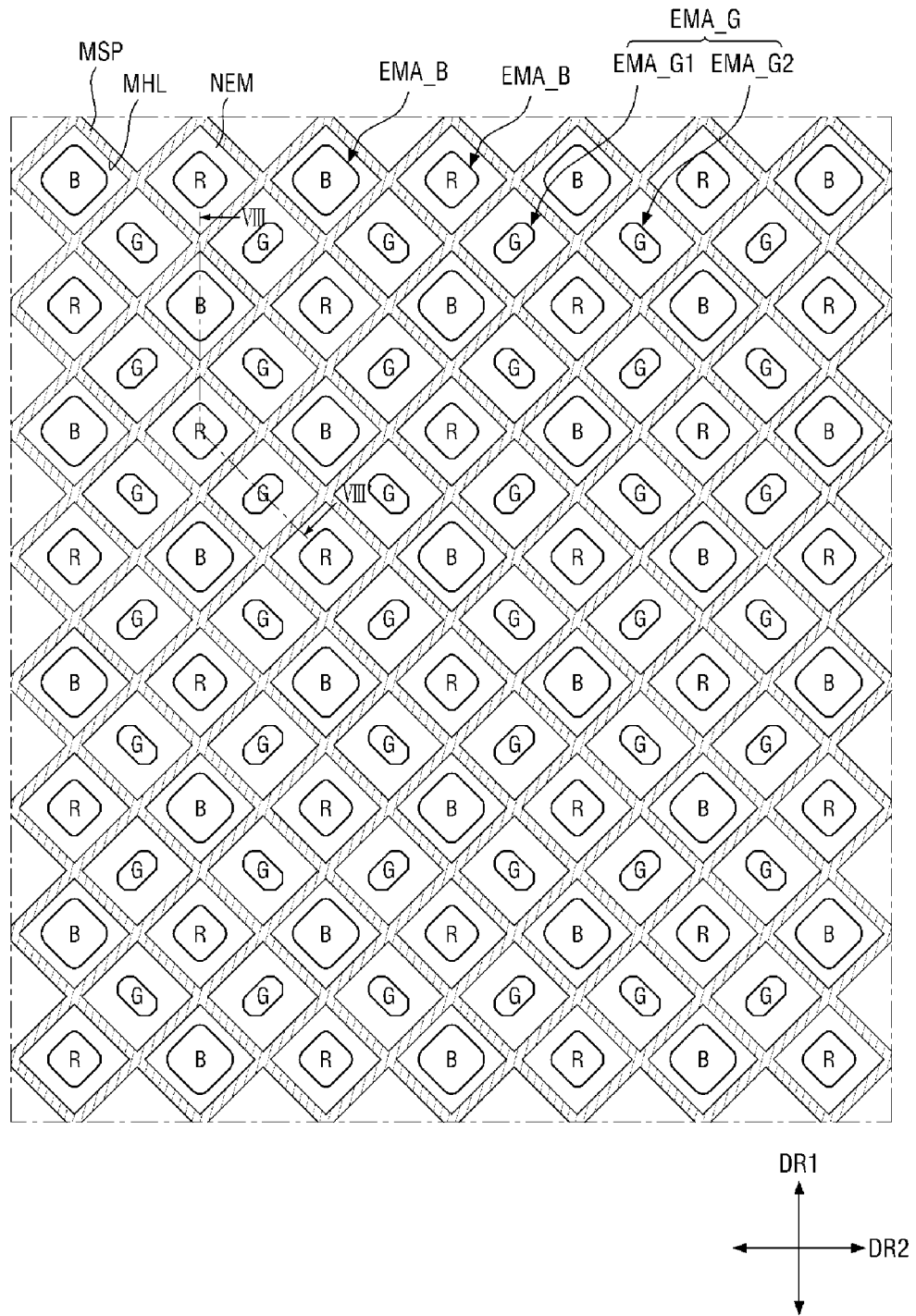
FIG. 7 is a layout view illustrating the relative arrangement relationship between pixels of a display unit and a mesh pattern of a touch member according to an embodiment.

The first sensor portion SP1 of the first sensing electrode IE1 and the second sensor portion SP2 of the second sensing electrode IE2 may each include a planar pattern or a mesh pattern. When each of the first sensor portion SP1 and the second sensor portion SP2 includes a planar pattern, the first sensor portion SP1 and the second sensor portion SP2 may be made of a transparent conductive layer. When each of the first sensor portion SP1 and the second sensor portion SP2 includes a mesh pattern positioned along the non-light emitting area, as illustrated in FIGS. 5 and 7, the progress of emitted light may be without a substantial interference, even when opaque low-resistance metal is applied. Hereinafter, a case where each of the first sensor portion SP1 and the second sensor portion SP2 includes a mesh pattern will be described as an example, but the present disclosure is not limited thereto.

The first connection portion CP1 may connect the rhombic or triangular edge portions of the neighboring first sensor portions SP1. The second connection portion CP1 may connect the rhombic or triangular edge portions of the neighboring second sensor portions SP2. The widths (e.g., diagonals) of the first connection portion CP1 and the second connection portion CP2 may be smaller than the widths (e.g., diagonals) of the first sensor portion SP1 and the second sensor portion SP2.

The first sensing electrode IE1 and the second sensing electrode IE2 may be insulated from each other and may cross each other. The first sensing electrode IE1 and the second sensing electrode IE2 may be insulated from each other by connecting the first sensing electrode IE1 and the second sensing electrode IE2 through conductive layers located on different layers (levels) in areas crossing each other. The insulating and crossing of the first sensing electrode IE1 and the second sensing electrode IE2 may be performed by the first connection portion CP1 and/or the second connection portion CP2. For the insulating and crossing of the first sensing electrode IE1 and the second sensing electrode IE2, at least one of the first connection portion CP1 or the second connection portion CP2 may be located on a different layer (level) from that of the first sensing electrode IE1 and the second sensing electrode IE2.

For example, the first sensor portion SP1 of the first sensing electrode IE1 and the second sensor portion SP2 of the second sensing electrode IE2 may be formed of a conductive layer located on the same layer (level), and the first sensor portion SP1 and the second sensor portion SP2 themselves may not cross or overlap each other. The adjacent first sensor portion SP1 and the second sensor portion SP2 may be physically spaced apart from each other.

The second connection portion CP2 may be formed of the same conductive layer (e.g., may lie in (or be part of) the same layer) as the second sensor portion SP2, to connect the adjacent second sensor portions SP2. The adjacent first sensor portions SP1 of the first sensing electrode IE1 may be physically spaced apart from each other based on the area where the second connection portion CP2 passes. The first connection portion CP1 connecting the first sensor portions SP1 may be formed of a different conductive layer (e.g., may lie in (or be part of) a different layer) from that of the first sensor portion SP1, and may cross the region of the second sensing electrode IE2. The first connection portion CP1 may be electrically connected to each adjacent first sensor portion SP1 through a contact.

A plurality of first connection portions CP1 may be provided. For example, while the present disclosure is not limited thereto, the first connection portion CP1 may include one first connection portion CP1_1 overlapping and passing through the second sensor portion SP2 adjacent to one side of the first sensing electrode IE1, and another first connection portion CP1_2 overlapping and passing through the second sensing electrode IE2 adjacent to the other side of the first sensing electrode IE1. When a plurality of first connection portions CP1 are provided to connect two adjacent first sensor portions SP1, even if any one of the plurality of first connection portions CP1 is disconnected by static electricity and/or the like, the disconnection of the corresponding first sensing electrode IE1 may be prevented (or the risk thereof may be substantially reduced).

The first sensor portions SP1 and the second sensor portions SP2 adjacent to each other may constitute a unit sensing area SUT (refer to FIG. 5). For example, based on the area where the first sensing electrode IE1 and the second sensing electrode IE2 cross each other, half of two adjacent first sensor portions SP1 and half of two adjacent second sensor portions SP2 may form a square or a rectangle. Here, the area defined by half of two adjacent first sensor portions SP1 and half of two adjacent second sensor portions SP2 may be one unit sensing area SUT. The plurality of unit sensing areas SUT may be arranged in a matrix direction (e.g., matrix formation).

In each unit sensing area SUT, the capacitance value between the first sensor portion SP1 and the second sensor portion SP2 adjacent to each other may be measured to determine whether a touch input is performed, and the corresponding position may be calculated as touch input coordinates. Touch sensing may be performed in a mutual cap method, but the present disclosure is not limited thereto.

Each unit sensing area SUT may be larger in size than the pixel. For example, one unit sensing area SUT may correspond to a plurality of pixels. The length of one side of the unit sensing area SUT may be in a range of 4 mm to 5 mm, but is not limited thereto.

A plurality of touch signal lines are arranged in the non-active area NAR that is outside of the touch area. The plurality of touch signal lines may extend from touch pad portions TPA1 and TPA2 located in the sub-area SR to the non-active area NAR of the main area MR through the bending area BR.

The plurality of touch signal lines include a plurality of touch driving lines TX and a plurality of touch sensing lines RX. In an embodiment, the plurality of touch signal lines may further include a touch ground line G and/or a touch antistatic line ES.

The plurality of touch driving lines TX may be connected to the first sensing electrode IE1. In an embodiment, the plurality of touch driving lines may be connected to one first sensing electrode IE1. For example, the touch driving lines TX may include first touch driving lines TX_1 (e.g., TX1_1, TX2_1, TX3_1, and TX4_1) connected to the lower end of the first sensing electrode IE1, and second touch driving lines TX_2 (e.g., TX1_2, TX2_2, TX3_2, and TX4_2) connected to the upper end of the first sensing electrode IE1. The first touch driving lines TX1_1, TX2_1, TX3_1, and TX4_1 may extend from a touch signal line pad portion TPA1 to one side of the first direction DR1 (e.g., upward) to be connected to the lower end of the first sensing electrode IE1. The second touch driving lines TX1_2, TX2_2, TX3_2, and TX4_2 may extend from the touch signal line pad portion TPA1 to one side of the first direction DR1 (e.g., upward), and may bypass the left edge of the touch area to be connected to the upper end of the first sensing electrode IE1.

The plurality of touch sensing lines RX may be connected to the second sensing electrode IE2. In an embodiment, one touch sensing line RX may be connected to one second sensing electrode IE2. Each of the touch sensing lines RX1, RX2, RX3, RX4, RX5, and RX6 extends from a touch signal line pad portion TPA2 to one side of the first direction DR1 (e.g., upward), and extends to the right edge of the touch area to be connected to the right end of the second sensing electrode IE2.

The touch antistatic lines ES may be provided at the outermost portion of the touch signal line. In an embodiment, the touch antistatic lines ES may include a first touch antistatic line ES1, a second touch antistatic line ES2, a third touch antistatic line ES3, and a fourth touch antistatic line ES4. The first to fourth touch antistatic lines ES may surround the touch area and the signal lines in a ring (or ring-like) shape.

The first touch antistatic line ES1 may cover the outer side of the touch signal line located at the right side thereof. The second touch antistatic line ES2 may cover the inner side of the touch signal line located at the right side thereof. The third touch antistatic line ES3 may cover the inner side of the touch signal line located at the left side thereof and the outer side of the touch signal line extending from the lower side of the touch area in the second direction DR2. The fourth touch antistatic line ES4 may cover the outer side of the touch signal line located at the left side thereof and the outer side of the touch signal line extending from the upper side of the touch area in the second direction DR2.

The touch ground lines G may be provided between the signal lines. The touch ground lines G may include a first touch ground line G1, a second touch ground line G2, a third touch ground line G3, a fourth touch ground line G4, and a fifth touch ground line G5. The first touch ground line G1 may be between the touch sensing line RX and the first touch antistatic line ES1. The second touch ground line G2 may be between the second touch antistatic line ES and the touch sensing line RX. The third touch ground line G3 may be between the first touch driving lines TX_1 and the third touch antistatic line ES3. The fourth touch ground line G4 may be between the first touch driving lines TX_1 and the second touch driving lines TX_2. The fifth touch ground line G5 may be between the second touch driving lines TX_2 and the fourth touch antistatic line ES4.

Explaining a laminate structure of the touch member, the touch member may include a base layer 205, a first touch conductive layer 210 on the base layer 205, a first touch insulating layer 215 on the first touch conductive layer 210, a second touch conductive layer 220 on the first touch insulating layer 215, and a second touch insulating layer 230 covering the second touch conductive layer 220.

For example, the first touch conductive layer 210 may be on the base layer 205. The first touch conductive layer 210 is covered by the first touch insulating layer 215. The first touch insulating layer 215 insulates the first touch conductive layer 210 from the second touch conductive layer 220. The second touch conductive layer 220 may be on the first touch insulating layer 215. The second touch insulating layer 230 may cover and protect the second touch conductive layer 220.

The base layer 205 may include an inorganic insulating material. For example, the base layer 205 may include a silicon nitride layer, a silicon oxy nitride layer, a silicon oxide layer, a titanium oxide layer, an aluminum oxide layer, and/or the like. In some embodiments, the base layer 205 may be replaced with a second inorganic film 193 constituting a thin film encapsulation layer to be described in more detail later.

Each of the first touch conductive layer 210 and the second touch conductive layer 220 may include a metal layer or a transparent conductive layer. The metal layer may include aluminum, titanium, copper, molybdenum, and/or silver and/or an alloy thereof. The transparent conductive layer may include a transparent conductive oxide (such as indium tin oxide (ITO), indium zinc oxide (IZO), zinc oxide (ZnO), and/or indium tin zinc oxide (ITZO)), a conductive polymer (such as PEDOT), metal nanowires, and/or graphene. As described above, when the first touch conductive layer 210 and the second touch conductive layer 220 are provided on the non-light emitting area, the progress of emitted light may have no substantial interference, even if the first touch conductive layer 210 and the second touch conductive layer 220 are made of a low-resistance opaque metal.

The first touch conductive layer 210 and/or the second touch conductive layer 220 may include a conductive layer having a multi-layer structure. For example, the first touch conductive layer 210 and/or the second touch conductive layer 220 may have a three-layer structure of titanium/aluminum/titanium.

In an embodiment, the first connection portion CP1 may be formed of the first touch conductive layer 210, and the first sensor portion SP1, the second sensor portion SP2, and the second connection portion CP2 may be formed of the second touch conductive layer 220. However, the present disclosure is not limited thereto. In some embodiments, the first connection portion CP1 may be formed of the second touch conductive layer 220, and the first sensor portion SP1, the second sensor portion SP2, and the second connection portion CP2 may be formed of the first touch conductive layer 210. The touch signal line may be formed of the first touch conductive layer 210 or the second touch conductive layer 220, and may also be formed of the first touch conductive layer 210 and the second touch conductive layer 220 connected by a contact. However, the touch conductive layer constituting each member of the sensing electrode or the signal line may be variously suitably modified.

The first touch insulating layer 215 and the second touch insulating layer 230 may each independently include an inorganic material or an organic material. In an embodiment, one of the first touch insulating layer 215 and the second touch insulating layer 230 may include an inorganic material, and the other thereof may include an organic material. In an embodiment, the first touch insulating layer 215 may include silicon nitride, silicon oxynitride, silicon oxide, titanium oxide, and/or aluminum oxide, and the second touch insulating layer 230 may include at least one of acrylic resin, methacryl resin, polyisoprene, vinyl resin, epoxy resin, urethane resin, cellulose resin, siloxane resin, polyimide resin, polyamide resin, or perylene resin.

The first touch insulating layer 215 may include a contact hole CNT_T. The first touch conductive layer 210 (for example, the first connection portion CP1) and a part of the second touch conductive layer 220 (for example, the first sensor portion SP1) may be electrically connected through the contact hole CNT_T.

FIG. 7 is a layout view illustrating the relative arrangement relationship between pixels of a display unit and a mesh pattern of a touch member according to an embodiment.

Referring to FIG. 7, the display area of the active area AAR includes a plurality of pixels. Each pixel includes a light emitting area EMA. The light emitting area EMA may overlap an opening of a bank layer 126 (see e.g., FIG. 8) and may be defined by the opening of the bank layer 126. The non-light emitting area NEM may be between the light emitting areas EMA of each pixel. The non-light emitting area NEM may overlap the bank layer 126 and may be defined by the bank layer 126. The non-light emitting area NEM may surround the light emitting area EMA. The non-light emitting area NEM has a grid shape or a mesh shape along a diagonal direction between (and crossing) the first direction DR1 and the second direction DR2 in a plan view. The mesh pattern MSP may be provided in the non-light emitting area NEM.

The pixel may include a first color pixel (for example, a red pixel), a second color pixel (for example, a blue pixel), and a third color pixel (for example, a green pixel). The first color may have a wavelength band ranging from about 640 nm to about 750 nm, which is perceived as red, the second color may have a wavelength band ranging from about 492 nm to about 600 nm, which is perceived as green, and the third color may have a wavelength band ranging from about 450 nm to about 480 nm, which is perceived as blue.

The shape of the light emitting area EMA of each color pixel may be an octagon, a quadrangle, or rhombus having rounded corners. However, the present disclosure is not limited thereto, and the shape of each light emitting area EMA may be any suitable shape, for example, a circle, a rhombus, a polygon, or a polygon having rounded corners.

In an embodiment, the shape of the light emitting area EMA_R of the first color pixel and the shape of the light emitting area EMA_B of the second color pixel may have similar shapes to each other, for example, a rhombus having rounded corners. The light emitting area EMA_B of the second color pixel may be larger than the light emitting area EMA_R of the first color pixel.

The light emitting area EMA_G of the third color pixel may be smaller than the light emitting area EMA_R of the first color pixel. The light emitting area EMA_G of the third color pixel may be inclined in a diagonal direction and have an octagonal shape having a maximum width in the inclined direction. The third color pixels may include a third color pixel in which the light emitting area EMA G1 is inclined in a first diagonal direction and a third color pixel in which the light emitting area EMA_G2 is inclined in a second diagonal direction.

The color pixels may be arranged in various suitable ways. In an embodiment, the first color pixels (for example, red pixels) and the second color pixels (for example, blue pixels) may be alternately arranged in a first row along the second direction DR2, and the third color pixels (for example, green pixels) may be arranged in a second row adjacent to the first row along the second direction DR2. The pixels (third color pixels) belonging to the second row may be alternately arranged in the second direction DR2 with respect to the pixels belonging to the first row. In the second row, the third color pixels inclined in a first diagonal direction (refer to EMA G1) and the third color pixels inclined in a second diagonal direction (refer to EMA_G2) may be alternately arranged along the second direction DR2. The number of the third color pixels belonging to the second row may be twice the number of the first color pixels or the second color pixels belonging to the first row.

The third row has the same arrangement of color pixels as the first row, but the arrangement order may be reversed. That is, the second color pixels may be arranged in the third row belonging to the same column as the first color pixels in the first row, and the first color pixels may be arranged in the third row belonging to the same column as the second color pixels in the first row. The fourth row has the same arrangement of the third color pixels as the second row, but the arrangement order may be reversed with respect to the shape inclined in the diagonal direction. That is, the third color pixels inclined in the second diagonal direction may be arranged in the fourth row belonging to the same column as the third color pixels inclined in the first diagonal direction of the second row, and the third color pixels inclined in the first diagonal direction may be arranged in the fourth row belonging to the same column as the third color pixels inclined in the second diagonal direction of the second row.

The arrangements of the first to fourth rows may be repeated along the first direction DR1. However, the arrangement of the pixels is not limited to the above illustration.

The mesh pattern MSP may be in the non-light emitting area NEM along the boundary of the pixels. The mesh pattern MSP may not overlap the light emitting area EMA. The width of the mesh pattern MSP may be smaller than the width of the non-light emitting area NEM. In an embodiment, the mesh hole MHL in the mesh pattern MSP may have a substantially rhombus shape.

Although in some embodiments, the sizes of the mesh holes MHL may be the same, they may also be different from each other depending on the size of the light emitting area EMA exposed by the mesh hole MHL, or may be different from each other regardless of the size of the light emitting area EMA. Although it is illustrated in the drawings that one mesh hole MHL corresponds to one light emitting area EMA, the present disclosure is not limited thereto, and one mesh hole MHL may correspond to two or more light emitting areas EMA.

Figure 8:
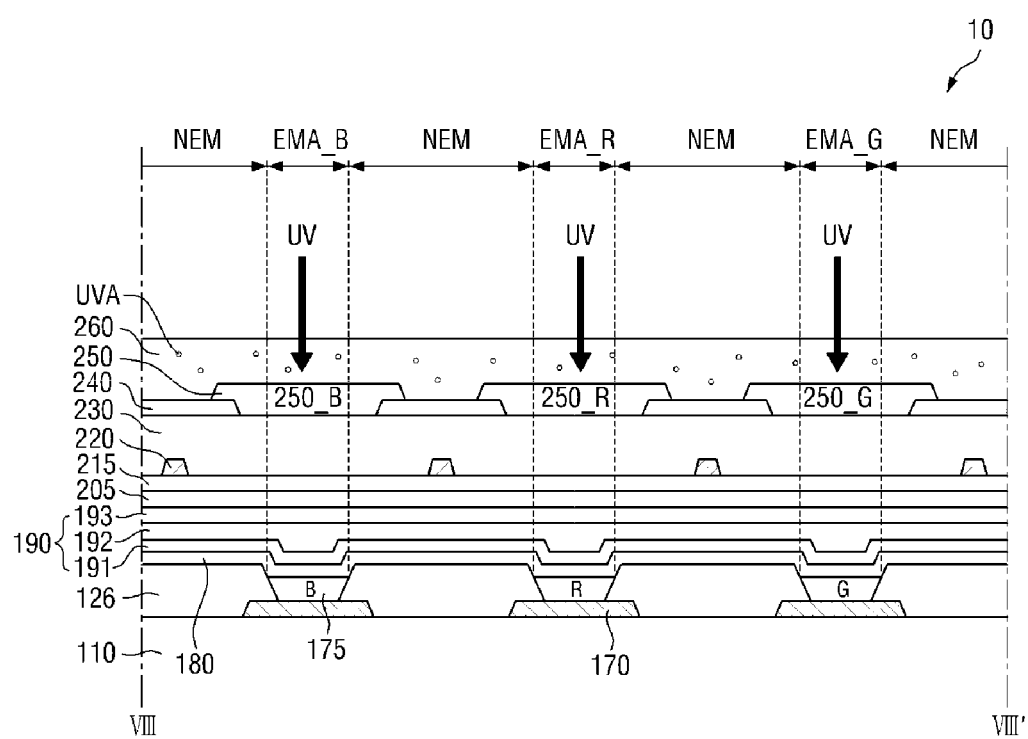
FIG. 8 is a cross-sectional view taken along line VIII-VIII' of FIG. 7.

FIG. 8 is a cross-sectional view taken along the line VIII-VIII' of FIG. 7.

In the cross-sectional view of FIG. 8, most of layers under an anode electrode 170 are omitted, and a structure of an upper portion of an organic light emitting diode is mainly illustrated.

Referring to FIG. 8, a substrate 110 of the display device 1 may be made of an insulating material such as a polymer resin. Examples of the polymer resin may include polyethersulfone (PES), polyacrylate (PA), polyarylate (PAR), polyetherimide (PEI), polyethylene naphthalate (PEN), polyethylene terephthalate (PET), polyphenylene sulfide: (PPS), polyallylate, polyimide (PI), polycarbonate (PC), cellulose triacetate (CAT), cellulose acetate propionate (CAP), and combinations thereof. The substrate 100 may be a flexible substrate capable of bending, folding, rolling, and/or the like. An example of the material forming (to form) the flexible substrate may include, but is not limited to, polyimide (PI).

An anode electrode 170 may be provided on the substrate 110. In the drawings, for convenience of explanation, a case where the anode electrode 170 is directly on the substrate 110 is illustrated. However, as is well known in the art, a plurality of thin film transistors and a plurality of signal lines may be arranged between the substrate 110 and the anode electrode 170.

The anode electrode 170 may be a pixel electrode provided for each pixel. The anode electrode 170 may have a laminated film structure in which a material layer having a high work function including indium-tin-oxide (ITO), indium-zinc-oxide (IZO), zinc oxide (ZnO), and/or induim oxide ($In_2O_3$), and a reflective material layer including silver (Ag), magnesium (Mg), aluminum (Al), platinum (Pt), lead (Pd), gold (Au), nickel (Ni), neodium (Nd), iridium (Ir), chromium (Cr), lithium (Li), calcium (Ca) or a mixture thereof, are laminated. The material layer having a higher work function may be provided over the reflective material layer and thus may be closer to the light emitting layer 175. The anode electrode 170 may have a multi-layer structure of ITO/Mg, ITO/MgF, ITO/Ag, or ITO/Ag/ITO, but the structure thereof is not limited thereto.

A bank layer 126 may be on the substrate 110. The bank layer 126 may be on the anode electrode 170, and may include an opening that exposes the anode electrode 170. The light emitting area EMA and the non-light emitting area NEM may be divided by the bank layer 126 and the opening thereof. The bank layer 126 may include an organic insulating material such as polyacrylate resin, epoxy resin, phenolic resin, polyamide resin, polyimide resin, unsaturated polyester resin), polyphenylene ether resin, polyphenylene sulfide resin, and/or benzocyclobutene (BCB). The bank layer 126 may include an inorganic material.

A light emitting layer may be provided on the anode 170 exposed by the bank layer 126. The light emitting layer may include an organic layer 175. The organic layer 175 may include an organic light emitting layer, and may further include a hole injection/hole transport layer and/or an electron injection/electron transport layer.

The wavelengths of light emitted by the light emitting layers 175 may be different for each color pixel. For example, the light emitting layers 175 may include a first color light emitting layer in the light emitting area EMA_R of the first color pixel, a second color light emitting layer in the light emitting area EMA_B of the second color pixel, and a third color light emitting layer in the light emitting area EMA_G of the third color pixel. The first color light emitting layer may emit light of a red wavelength band, the second color light emitting layer may emit light of a blue wavelength band, and the third color light emitting layer may emit light of a green wavelength band.

When each light emitting layer 175 is exposed to external light UV of a short wavelength band, the organic material constituting the light emitting layer 175 may be damaged. In the present specification, the light of a short wavelength band may refer to light of an ultraviolet wavelength band and/or light of a visible wavelength band close to the ultraviolet wavelength band.

When the organic materials constituting the light emitting layers 175 are damaged, the sizes of the light emitting areas EMA_R, EMA_G, and EMA_B on which the light emitting layers 175 are positioned may be reduced, causing not only does the overall luminous efficiency of the display device 1 to decrease, but also the luminous efficiencies of the light emitting layers 175 to decrease differently, so that abnormal colors may be expressed. Therefore, in the display device 1 according to an embodiment, a light absorber for absorbing external light of a short wavelength band may be further provided on (or above) the light emitting layer 175, thereby preventing or reducing a decrease in the overall luminous efficiency of the display device 1 and preventing or reducing the expression of abnormal colors. In an embodiment, the light absorber may be provided in an overcoat layer 260 (to be described in more detail later) to reduce the total amount of external light UV of a short wavelength band irradiated onto each light emitting layer 175.

A cathode electrode 180 may be provided on the organic layer 175. The cathode electrode 180 may be a common electrode entirely (e.g., integrally) provided on the organic layer 175 without distinguishing the pixels. The anode electrode 170, the organic layer 175, and the cathode electrode 180 may constitute an organic light emitting element.

The cathode electrode 180 not only may contact the organic layer 175 but also may contact the upper surface of the bank layer 126. In an area where a spacer 127 is formed, the cathode electrode 180 may contact the surface of the spacer 127, and may cover the surface of the spacer 127. The cathode electrode 180 may be conformally formed with respect to a lower structure (e.g., the cathode electrode 180 may conform to the shape of the underlying structure) to reflect the step of the lower structure.

The cathode electrode 180 may include a material layer having a low work function, for example, the material layer including Li, Ca, LiF/Ca, LiF/Al, Al, Mg, Ag, Pt, Pd, Ni, Au Nd, Ir, Cr, BaF, Ba, or a compound or mixture thereof (for example, a mixture of Ag and Mg). The cathode electrode 180 may further include a transparent metal oxide layer on the material layer having a low work function.

A thin film encapsulation layer 190 including a first inorganic film 191, an organic film 192, and a second inorganic film 193 may be provided on the cathode electrode 180. Each of the first inorganic film 191 and the second inorganic film 193 may include silicon nitride, silicon oxide, and/or silicon oxynitride. The organic film 192 may include an organic insulating material such as polyacrylate resin, epoxy resin, phenolic resin, polyamide resin, polyimide resin, unsaturated polyester resin), polyphenylene ether resin, polyphenylene sulfide resin, and/or benzocyclobutene (BCB).

A base layer 205, a first touch insulating layer 215, a second touch conductive layer 220, and a second touch insulating layer 230 may be sequentially positioned on the thin film encapsulation layer 190. Redundant description of each layer already described above will not be provided. Because FIG. 8 is a cross-sectional view of a sensor unit, the first touch conductive layer 210 is not shown in the cross-sectional view.

The second touch conductive layer 220 may overlap the bank layer 126, and may be positioned in the non-light emitting area NEM. The second touch conductive layer 220 constitutes the mesh pattern MSP of the sensor unit, and does not overlap the light emitting area EMA, so that the second touch conductive layer 220 does not interfere with light emission and may not be visible to the user.

A light blocking pattern 240 is provided on the second touch insulating layer 230. The light blocking pattern 240 may serve to reduce reflection of external light and improve reflection color. The light blocking pattern 240 may be in the non-light emitting area NEM. The light blocking pattern 240 may have a grid shape or a mesh shape in a plan view. The light blocking pattern 240, the touch conductive layers 210 and 220, and the bank layer 126 are all provided in the non-light emitting area NEM, and overlap each other in the thickness direction. The width of the light blocking pattern 240 may be less than or equal to the width of the bank layer 126, and may be greater than the width of each of the touch conductive layers 210 and 220. The light blocking pattern 240 may not overlap the light emitting area EMA.

A color filter layer 250 may be on the light blocking pattern 240. The color filter layer 250 may serve to block or reduce light of a color other than the corresponding colors in each color pixel. The color filter layer 250 may be provided on one surface of the second touch insulating layer 230 exposed through the opening of the light blocking pattern 240. In addition, the color filter layer 250 may be partially on the light blocking pattern 240 adjacent thereto.

The color filter layer 250 may include a blue color filter layer 250_13 in the second color pixel, a red color filter layer 250_R in the first color pixel, and a green color filter layer 250_G in the third color pixel. Each color filter layer 250 may include a colorant, such as a dye and/or a pigment, that absorbs wavelengths other than the corresponding color wavelength. The blue color filter layer 250_13 may transmit light of a wavelength band corresponding to the second color and may absorb light in any wavelength band except for that of the second color, and the red color filter layer 250_R may transmit light of a wavelength band corresponding to the first color or more. For example, the red color filter layer 250_R may further transmit light of a wavelength band of about 350 nm to about 380 nm, depending on the constituent material, but the transmission amount thereof may be significantly smaller than that of light of a wavelength band corresponding to the first color. The red color filter layer 250_R may absorb light other than the light of the first color wavelength band and the light of the wavelength band of about 350 nm to about 380 nm. The green color filter layer 250_G may transmit the light of the third color and absorb light of a wavelength band other than the third color.

Although it is shown in the drawings that neighboring color filter layers 250 are provided on the light blocking pattern 240 to be spaced apart from each other, the neighboring color filter layers 250 may partially overlap each other on the light blocking pattern 240.

In a comparable device, the color filter layer 250 may be damaged when the color filter layer 250 is exposed to external light UV of a short wavelength band (for example, light of an ultraviolet wavelength band). More specifically, when the color filter layer 250 is exposed to external light UV of a short wavelength band, each of the red color filter layers 250_R may be damaged, so that the red color filter layer 250_R may transmit light of a wavelength band of about 350 nm to about 380 nm more than before the damage, and the red color filter layer 250_R may transmit light of a wavelength band corresponding to the second color less than before the damage.

However, in the display device 1 according to an embodiment, a light absorber for absorbing external light of a short wavelength band may be further provided on (above) the light emitting layer 175, thereby preventing or reducing the damage of the color filter layer 250.

An overcoat layer 260 is provided on the light blocking pattern 240 and the color filter layer 250. The overcoat layer 260 may be provided directly on the light blocking pattern 240 and the color filter layer 250. The overcoat layer 260 serves to cover and protect the light blocking pattern 240 and the color filter layer 250. According to an embodiment, the overcoat layer 260 may further serve to planarize the surface. The overcoat layer 260 may include an organic insulating material.

Examples of the organic insulating material may include polyacrylate resin, epoxy resin, phenolic resin, polyamide resin, polyimide resin, unsaturated polyester resin), polyphenylene ether resin, polyphenylene sulfide resin, and benzocyclobutene (BCB).

The overcoat layer 260 may further include a light absorber UVA dispersed in the overcoat layer 260.

In the present specification, the term "substituted or unsubstituted" may refer to a group that is unsubstituted or that is substituted with at least one substituent selected from the group consisting of a deuterium atom, a halogen atom, a cyano group, a nitro group, an amino group, a silyl group, a boron group, a phosphine oxide group, a phosphine sulfide group, an alkyl group, an alkenyl group, an aryl group, and a heterocyclic group. Each of the aforementioned substituents may itself be substituted or unsubstituted. For example, a biphenyl group may be interpreted as an aryl group, or may be interpreted as a phenyl group substituted with a phenyl group.

In the present specification, examples of the halogen atom may include a fluorine atom, a chlorine atom, a brome atom, and an iodine atom.

In the present specification, the alkyl group may be linear, branched, or cyclic alkyl group. The number of carbon atoms in the alky group may be 1 to 30, 1 to 20, 1 to 10, or 1 to 6. Examples of the alkyl group may include, but are not limited to, methyl group, ethyl group, n-propyl group, isopropyl group, an n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, cyclopentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hex Sildecyl group, 2-octyldecyl group, n-undecyl group, n-dodecyl group, 2-ethyldodecyl group, 2-butyldodecyl group, 2-hexyldodecyl group, 2-octyldodecyl group, n-tridecyl group, n-tetradecyl, n-pentadecyl group, n-hexadecyl group, 2-ethylhexadecyl group, 2-butylhexadecyl group, 2-hexyl hexadecyl group, 2-octylhexadecyl group, n-heptadecyl group, n-octadecyl group, n-nonadecyl group, n-icosyl group, 2-ethyl-icosyl group, 2-butyl-icosyl group, 2-hexyl-icosyl group, 2-octyl-icosyl group, n-henoxyl group, n-docosyl group, n-tricosyl group, n-tetracosyl group, n-pentacosyl group, n-hexacosyl group, n-heptacosyl group, n-octacosyl group, n-nonacosyl group, and n-triacontyl group.

In the present specification, the alkenyl group may be linear or branched. The number of carbon atoms in the alkenyl group is not particularly limited, but may be 2 to 30, 2 to 20, or 2 to 10. Examples of the alkenyl group may include, but are not limited to, vinyl group, 1-butenyl group, 1-pentenyl group, 1,3-butadienyl aryl group, styrenyl group, and styryl vinyl group.

In the present specification, the aryl group may refer to any functional group or substituent group derived from an aromatic hydrocarbon ring. The aryl group may be a monocyclic aryl group or a polycyclic aryl group. The number of ring-forming carbon atoms in the aryl group may be 6 to 60, 6 to 30, 6 to 20, or 6 to 15. Examples of the aryl group may include, but are not limited to, phenyl group, naphthyl group, fluorenyl group, anthracenyl group, phenanthryl group, biphenyl group, terphenyl group, quarterphenyl group, quinquephenyl group, sexaphenyl group, biphenylene group, triphenylene group, pyrenyl group, benzo fluoranthenyl group, and chrysenyl group.

In the present specification, the fluorenyl group may be substituted, and two substituents may be bonded to each other to form a spiro structure. Examples of the case where the fluorenyl group is substituted are as follows. However, the present disclosure is not limited thereto.

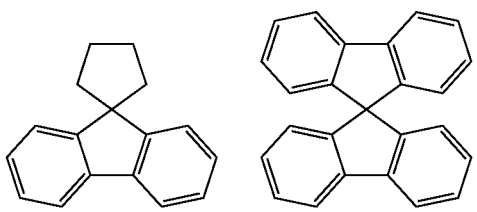

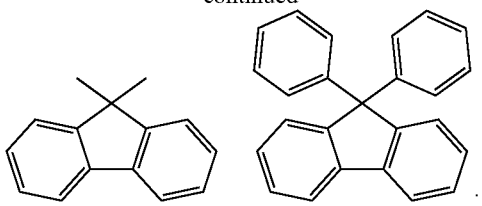

In the present specification, the heteroaryl group may be a heteroaryl group including at least one of O, N, P, Si, or S as a hetero atom. When the heteroaryl group includes two hetero atoms, the two hetero atoms may be the same as or different from each other. The number of ring-forming carbon atoms in the heteroaryl group may be 2 to 60, 2 to 30, or 2 to 20. The heteroaryl group may be a monocyclic heteroaryl group or a polycyclic heteroaryl group. The polycyclic heteroaryl group may have, for example, a bicyclic or tricyclic structure. Examples of the heteroaryl group may include, but are not limited to, thiophene group, furan group, pyrrole group, imidazole group, thiazole group, oxazole group, oxadiazole group, triazole group, pyridine group, bipyridine group, pyrimidine group, triazine group, triazole group, acridine group, pyridazine group, pyrazine group, quinoline group, quinazoline group, quinoxaline group, phenoxazine group, phthalazine group, pyrido pyrimidine group, pyrido pyrazine group, pyrazino pyrazine group, isoquinoline group, indole group, carbazole group, N-aryl carbazole group, N-heteroaryl carbazole group, N-alkylcarbazole group, benzoxazole group, benzoimidazole group, benzothiazole group, benzocarbazole group, benzothiophene group, dibenzothiophene group, thienothiophene group, benzofuran group, phenanthroline group, thiazole group, isoxazole group, oxadiazole group, thiadiazole group, phenothiazine group, dibenzosilole group, and dibenzofuran group.

In the present specification, the silyl group includes an alkyl silyl group and/or an aryl silyl group. Examples of the silyl group may include, but are not limited to, trimethylsilyl group, triethylsilyl group, t-butyldimethylsilyl group, vinyldimethylsilyl group, propyldimethylsilyl group, triphenylsilyl group, diphenylsilyl group, and phenylsilyl group.

In the present specification, the boron group includes an alkyl boron group and an aryl boron group. Examples of the boron group may include, but are not limited to, trimethyl boron group, triethyl boron group, t-butyl dimethyl boron group, triphenyl boron group, diphenyl boron group, and phenyl boron group.

In the present specification, the number of carbon atoms in the amino group is not particularly limited, but may be 1 to 30. The amino group may include an alkyl amino group and an aryl amino group. Examples of the amino group may include, but are not limited to, methylamino group, dimethylamino group, phenylamino group, diphenylamino group, naphthylamino group, 9-methyl-anthracenylamino group, and triphenylamino group.

In the present specification, the phosphine oxide group may be substituted with at least one of, for example, an alkyl group or an aryl group. Examples of the phosphine oxide group may include, but are not limited to, phenyl phosphine oxide group and diphenyl phosphine oxide group.

In the present specification, the number of carbon atoms in the carbonyl group is not particularly limited, but may be 1 to 30.

In the present specification, the alkoxy group may be linear, branched, or cyclic. The number of carbon atoms in the alkoxy group may be 1 to 30, 1 to 20, or 1 to 10. Examples of the alkoxy group may include, but are not limited to, methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, cyclohexyloxy, 3,3-dimethylbutyloxy, 2-ethylbutyloxy, n-octyloxy, n-nonyloxy, n-decyloxy, benzyloxy, and p-methylbenzyloxy.

In the present specification, the number of carbon atoms in the acrylate may be 1 to 20 or 1 to 10. The alkyl moiety of the acrylate may be a substituted or unsubstituted alkyl group and/or cycloalkyl group.

The light absorber UVA according to an embodiment is represented by Formula 1.

X—Ar—Y,  Formula 1

In Formula 1, Ar is pyrene, chrysene, or anthracene.

In Formula 1, Y is a hydrogen atom, a substituted or unsubstituted alkyl group having 1 to 20 carbon atoms, a substituted or unsubstituted alkenyl group having 2 to 20 carbon atoms, a substituted or unsubstituted alkoxy group having 1 to 20 carbon atoms, a substituted or unsubstituted acrylate group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted carbonyl group, a substituted or unsubstituted benzophenone group, a substituted or unsubstituted benzoate group, or a substituted or unsubstituted salicylate.

In Formula 1, X may be represented by any one of Formulae 2-1 to 2-3.

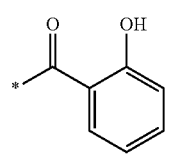

Formula 2-1

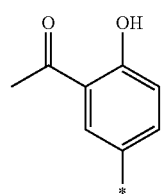

Formula 2-2

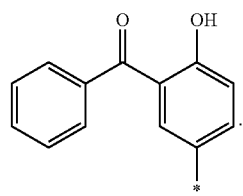

Formula 2-3

In Formulae 2-1 to 2-3, ⁎ refers to a binding site to Ar of Formula 1.

Formula 1 may be represented by any one of Formulae 1-1 to 1-3.

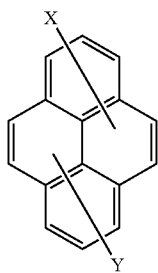

Formula 1-1

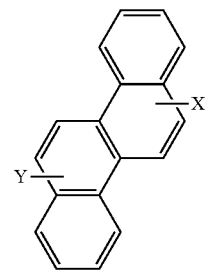

Formula 1-5

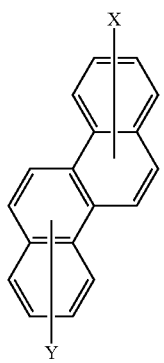

Formula 1-2

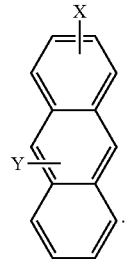

Formula 1-6

In Formulae 1-4 to 1-6, X and Y are the same as described above.

Formula 1-1 may be represented by Formula 1-7, Formula 1-2 may be represented by Formula 1-8, and Formula 1-3 may be represented by Formula 1-9. However, substitution positions of X and Y are not limited thereto.

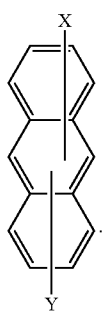

Formula 1-3

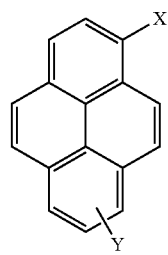

Formula 1-7

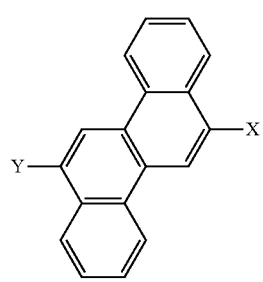

Formula 1-8

In Formulae 1-1 to 1-3, X and Y are the same as described above.

Formula 1-1 may be represented by Formula 1-4, Formula 1-2 may be represented by Formula 1-5, and Formula 1-3 may be represented by Formula 1-6.

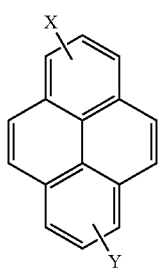

Formula 1-4

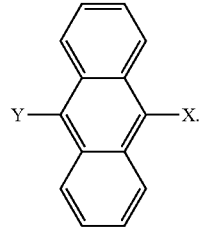

Formula 1-9

In Formulae 1-7 to 1-9, X and Y are the same as described above.

Formula 1-7 may be represented by any one of Formulae 1-10 to 1-12.

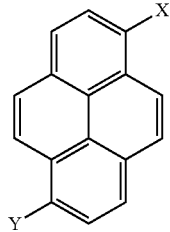

Formula 1-10

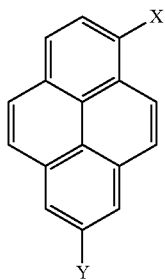

Formula 1-11

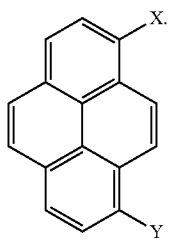

Formula 1-12

In Formulae 1-10 to 1-12, X and Y are the same as described above.

Although not limited thereto, Ar in Formula 1 may be pyrene.

In Formula 1, Y may be a hydrogen atom. In this case, Ar in Formula 1 may be substituted with only X.

In Formula 1, Y may be a substituted or unsubstituted aryl group having 6 to 15 ring-forming carbon atoms, or a substituted or unsubstituted polycyclic heteroaryl group.

In Formula 1, Y may be a substituted or unsubstituted phenyl group, a substituted or unsubstituted biphenyl group, a substituted or unsubstituted naphthyl group, a substituted or unsubstituted anthracene group, a substituted or unsubstituted phenanthrene group, a substituted or unsubstituted dibenzofuran group, or a substituted or unsubstituted dibenzothiophene group.

In Formula 1, when Y is a substituted phenyl group or a substituted biphenyl group, the substituent may be an alkoxy group having 1 to 10 carbon atoms.

In Formula 1, Y may be represented by Formula 3.

Formula 3

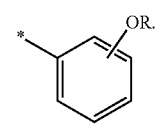

In Formula 3, R may be a substituted or unsubstituted alkyl group having 1 to 5 carbon atoms. For example, R may be a substituted or unsubstituted methyl group.

Formula 3 may be represented by Formula 3-1 or Formula 3-2.

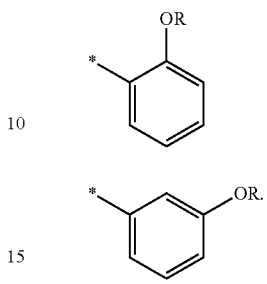

Formula 3-1

Formula 3-2

In Formulae 3-1 and 3-2, R is the same as described above.

Although not limited thereto, X may be represented by Formula 2-1, and Y may be represented by Formula 3.

Formula 1 may be represented by, for example, Formula 1-13.

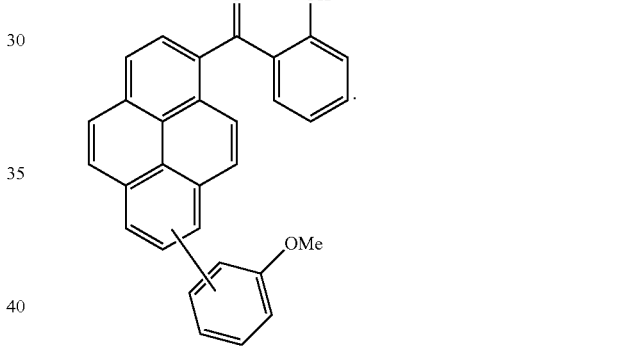

Formula 1-13

In Formula 1, Y may be represented by any one of Structural Formulae

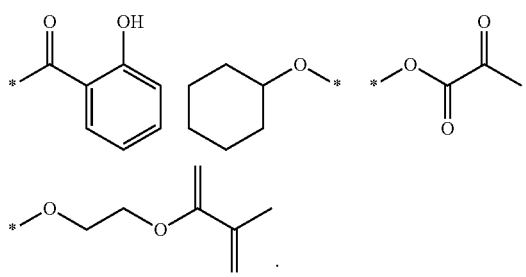

below:

In the Structural Formulae, ----* refers to a binding site to Ar in Formula 1.

The light absorber represented by Formula 1 according to an embodiment of the present disclosure may be any one selected from the compounds represented by Compound Group 1.

Compound Group 1
1
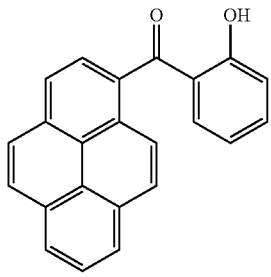
2
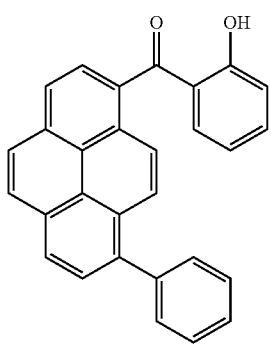
3
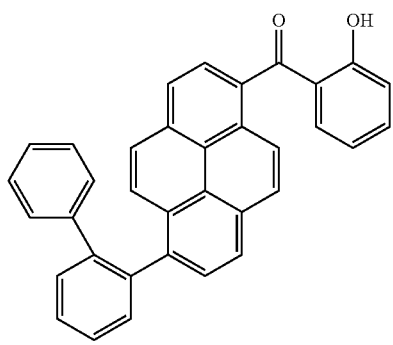
4
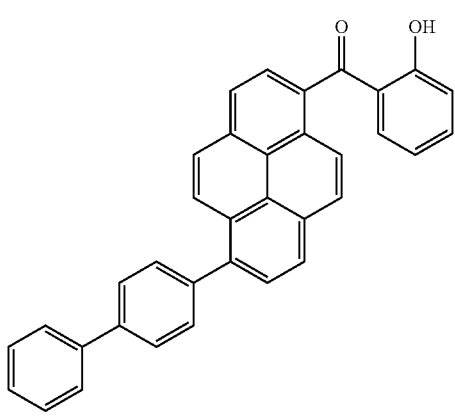
5
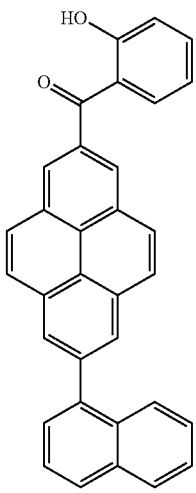
6
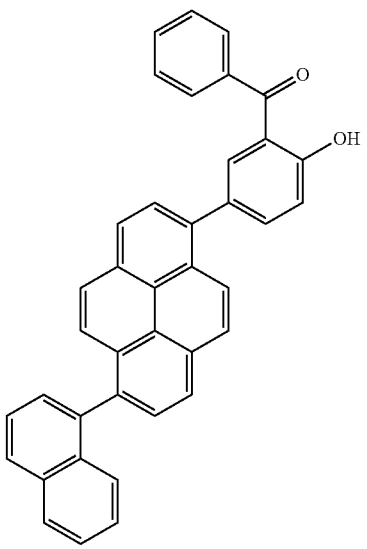
7
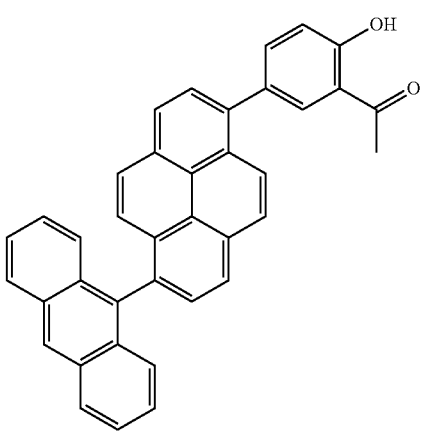

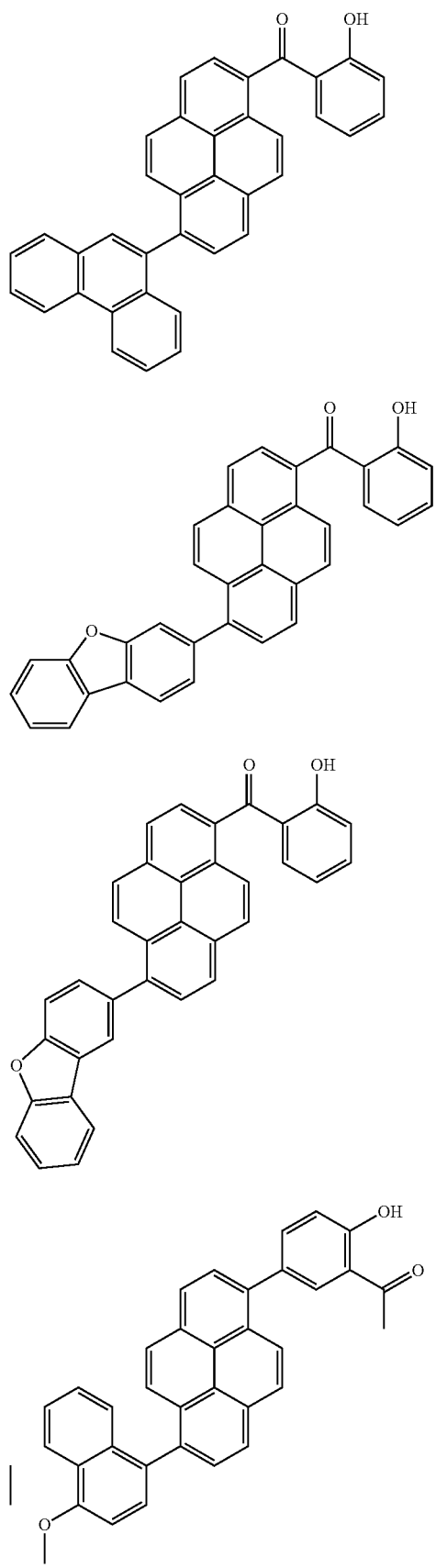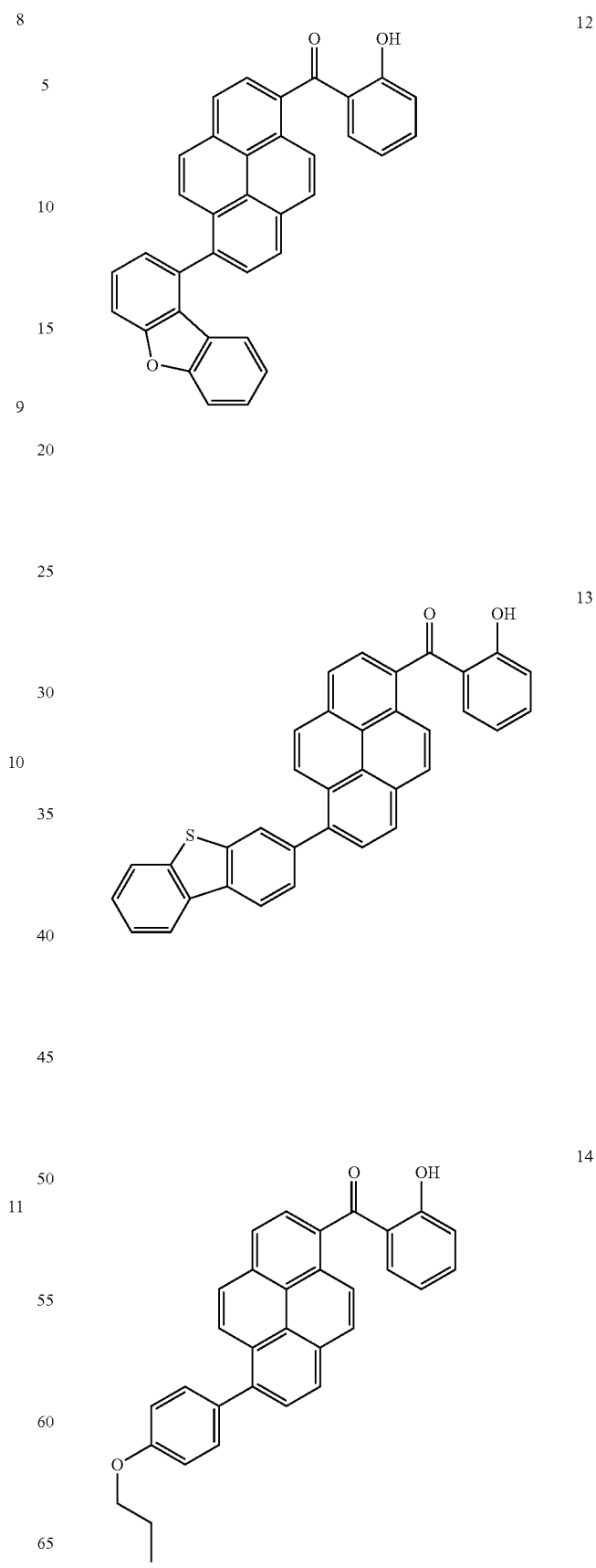

45
-continued
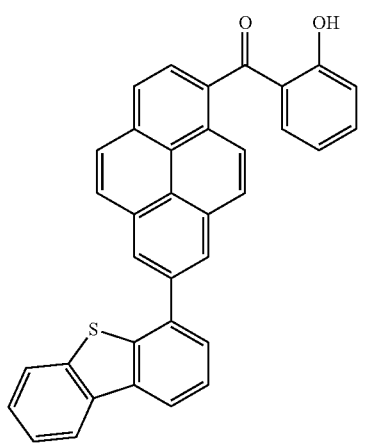
15
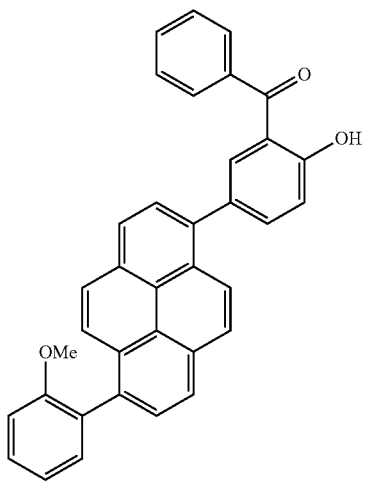
16
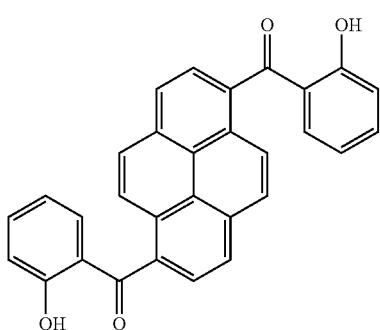
17
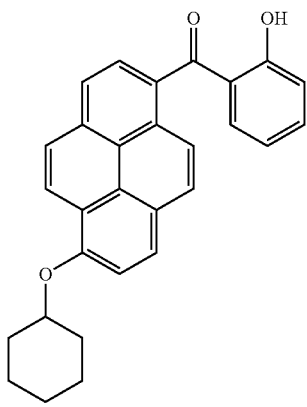
18
46
-continued
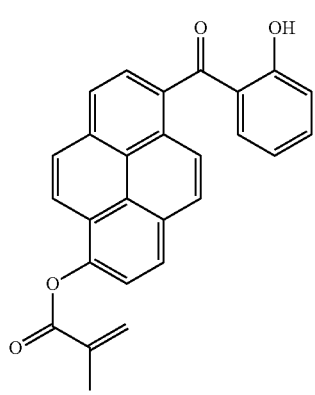
19
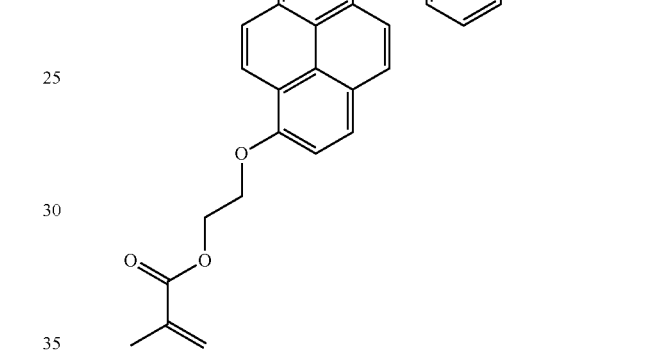
20
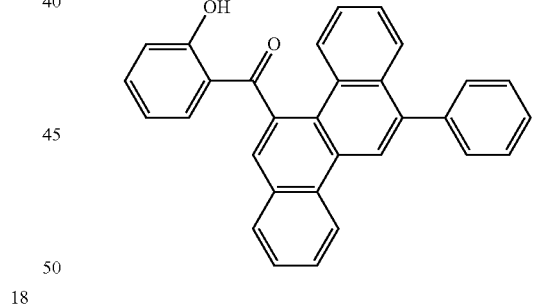
21
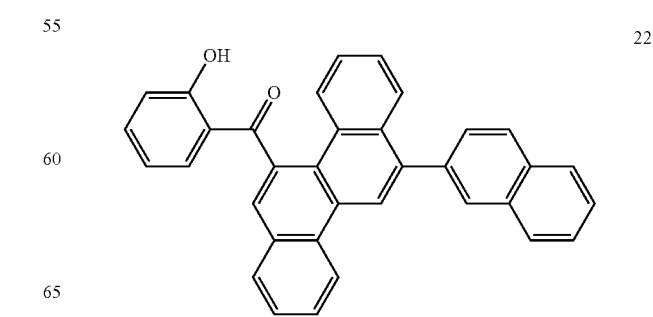
22

23
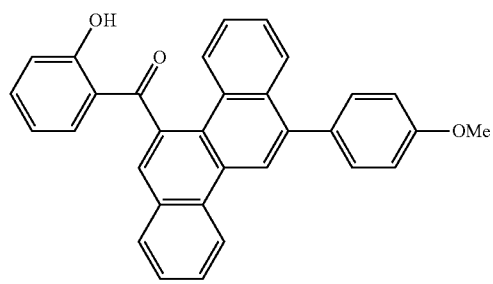
24
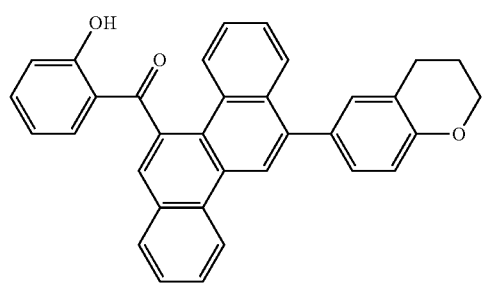
25
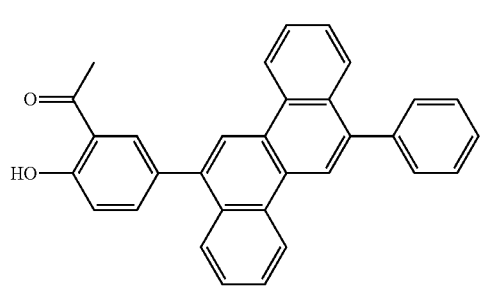
26
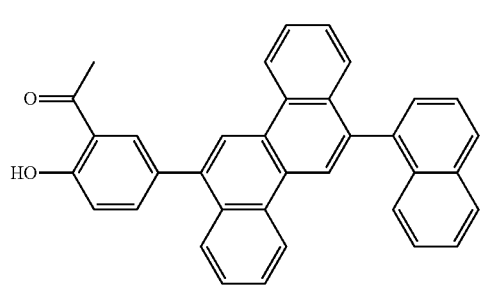
27
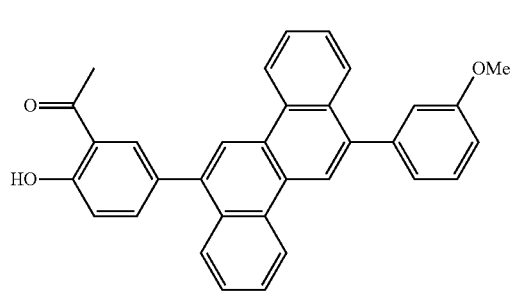
28
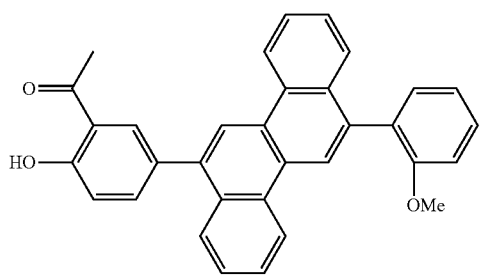
29
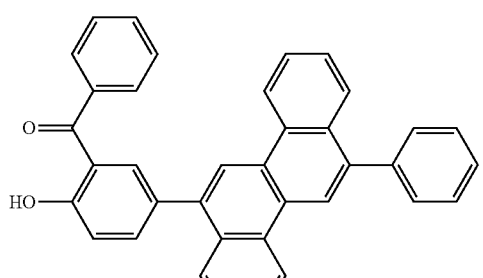
30
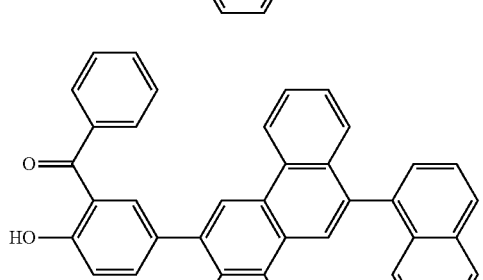
31
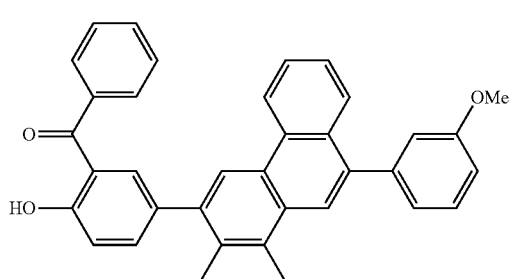
32
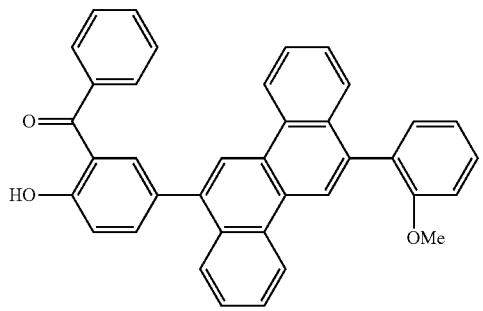

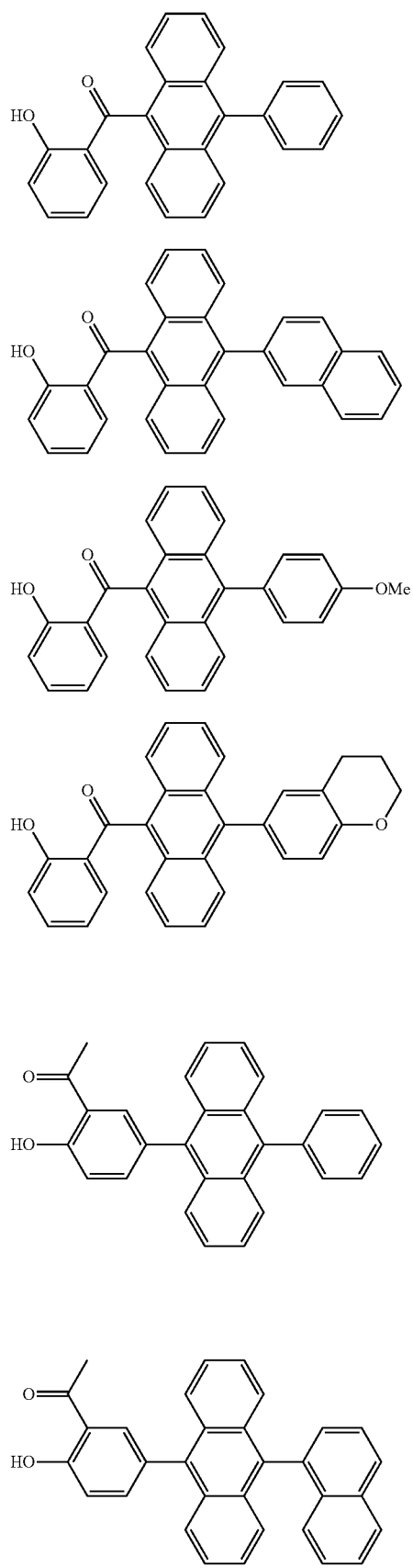
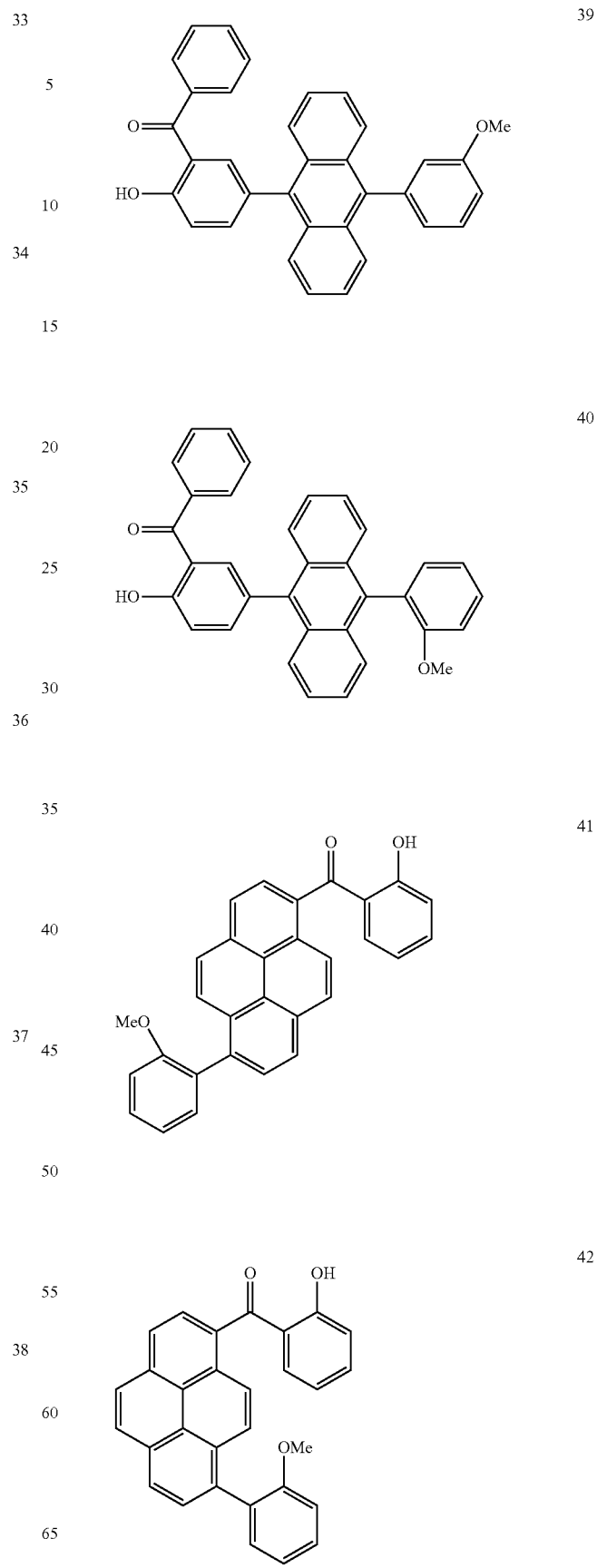

-continued

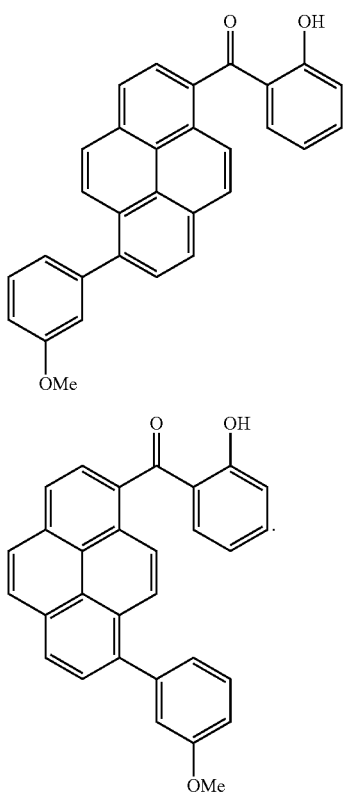

43

44

The content of the light absorber UVA represented by Formula 1 according to an embodiment in the overcoat layer 260 may be 3% to 25%.

As described above, according to an embodiment, when the light absorber UVA is further provided in the overcoat layer 260, the total amount of external light (UV) of a short wavelength band applied to each light emitting layer 175 may be reduced, so that a decrease in the overall luminous efficiency of the display device 1 may be prevented or reduced, and abnormal color expression may be prevented or reduced. In addition, damage of the color filter layer 250 may be prevented or reduced, thereby making the light transmitting function of each color filter layer 250 in the corresponding wavelength band better.

Figure 9:
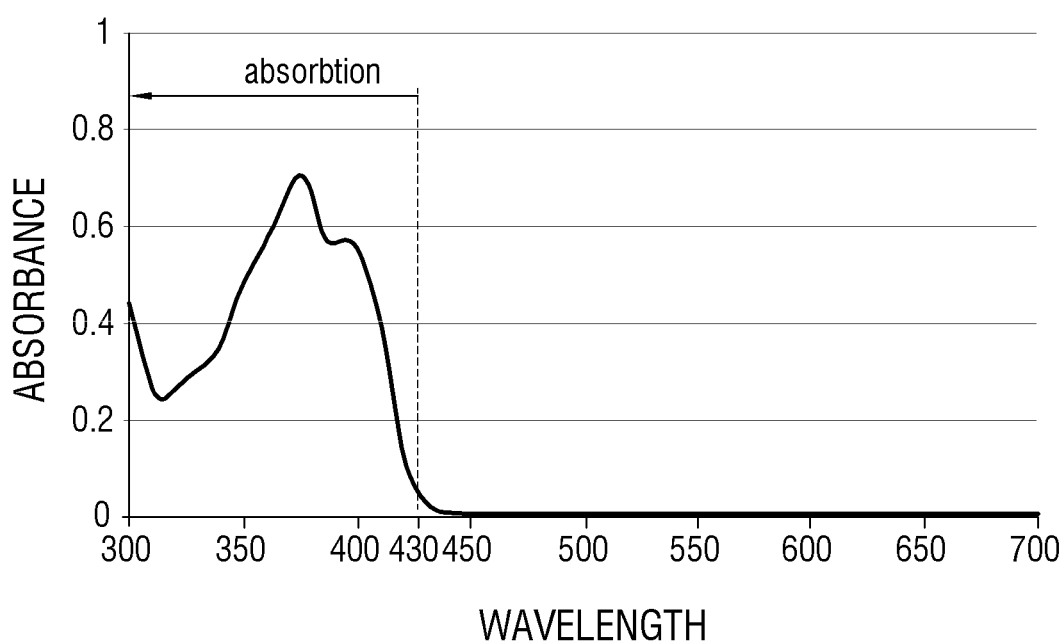
FIG. 9 is a graph illustrating the absorbance of a light absorber with respect to wavelength according to an embodiment.
Figure 10:
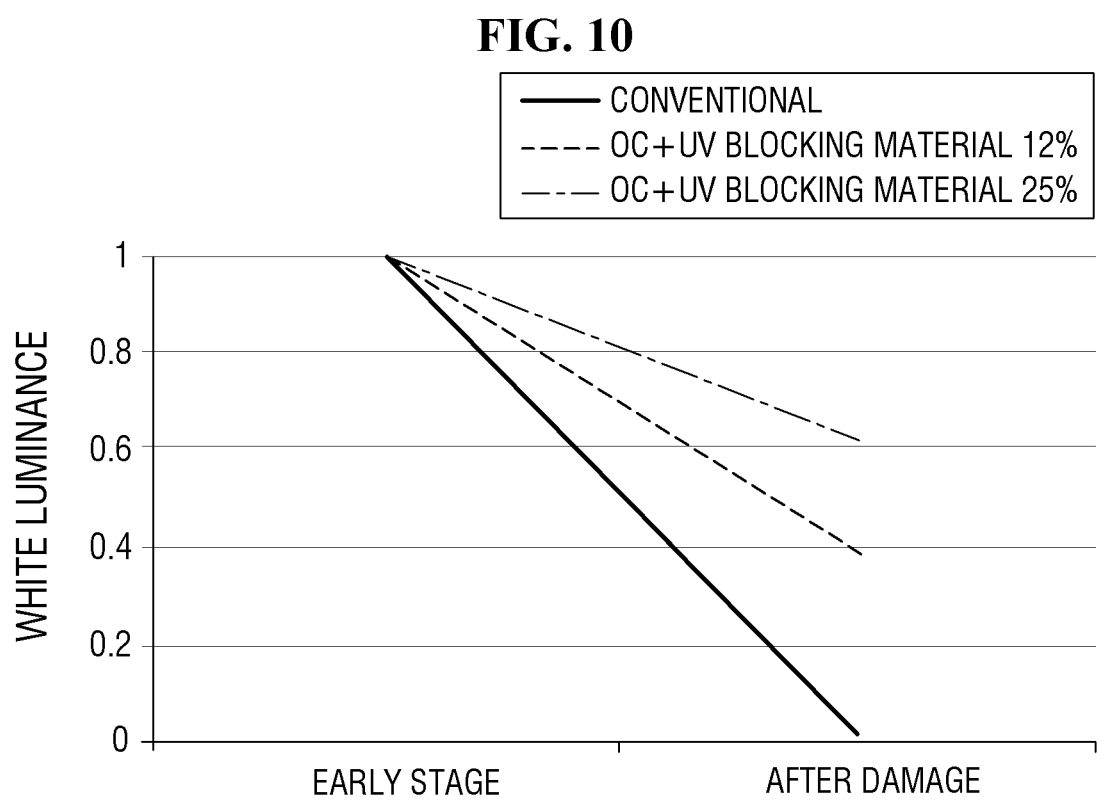
FIG. 10 is a graph illustrating the change rate of white luminance of a light emitting element in an overcoat layer according to the content of a light absorber.
Figure 11:
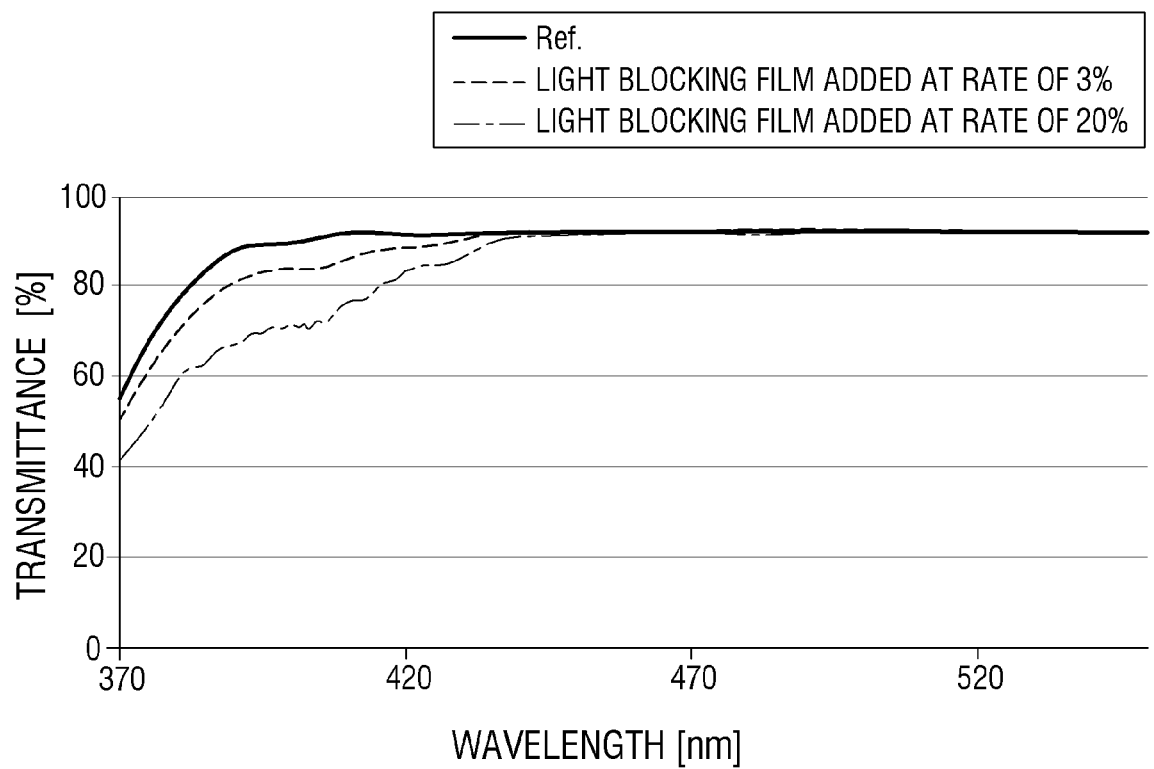
FIG. 11 is a graph illustrating the transmittance of light in an overcoat layer with respect to wavelength according to the content of a light absorber.

FIG. 9 is a graph illustrating the absorbance of a light absorber with respect to wavelength according to an embodiment, FIG. 10 is a graph illustrating the change rate of white luminance of a light emitting element in an overcoat layer according to the content of a light absorber, FIG. 11 is a graph illustrating the transmittance of light in an overcoat layer with respect to wavelength according to the content of a light absorber, and FIGS. 12 to 17 are graph illustrating the transmittances of light of red, green, and blue wavelength bands in an overcoat layer not including a light absorber and an overcoat layer including a light absorber.

First, referring to FIG. 9, the light absorber UVA represented by Formula 1 may have a maximum absorption wavelength of 380 nm to 410 nm. For example, the light absorber UVA represented by Formula 1 may have an absorbance of 0.7 or more in a wavelength band of 380 nm to 410 nm. In some embodiments, the light absorber represented by Formula 1 may have an absorbance of 0.8 or more, or 0.85 or more, in a wavelength band of 380 nm to 410 nm.

FIG. 10 illustrates the change rate of white luminance of a light emitting layer in an overcoat layer according to the content of a light absorber. Here, an overcoat layer not including the light absorber as a first sample, an overcoat layer including 12% of the light absorber as a second sample, and an overcoat layer including 25% as the light absorber as a third sample were prepared. The white efficiency of each sample before being irradiated with short-wavelength light having a wavelength band of 380 nm to 410 nm is measured as 1. Subsequently, each sample is irradiated with short-wavelength light having a wavelength band of 380 nm to 410 nm for a long period of time. As a result, it may be found that the first sample, which is an overcoat layer containing no light absorber at all, has a white efficiency decreasing substantially close to zero, the overcoat layer including 12% of the light absorber, which is the second sample, has a white luminance efficiency of about 0.4 and a decrease in white luminance by about 60% from before the irradiation of short-wavelength light, and the overcoat layer including 25% of the light absorber, which is the third sample, has a white luminance efficiency of about 0.65 and a decrease in white luminance by about 35% from before the irradiation of short-wavelength light. Accordingly, it may be found that the efficiency of the light emitting layer of the overcoat layer containing the light absorber is remarkably (relatively) high.

FIG. 11 shows the transmittance of external short-wavelength light with respect to wavelength according to the content of the light absorber represented by Formula 1 included in the overcoat layer.

Here, an overcoat layer not including the light absorber at all as a first sample, an overcoat layer including 3% of the light absorber as a second sample, and an overcoat layer including 20% as the light absorber as a third sample were prepared. Subsequently, each sample is irradiated with short-wavelength light having a wavelength band of 380 nm to 410 nm for a long period of time. As a result, it was found that the first sample, which is an overcoat layer not including the light absorber, has a short-wavelength light transmittance of about 80% to 90%, the overcoat layer including 3% of the light absorber, which is the second sample, has a short-wavelength light transmittance of about 70% to 83%, and the overcoat layer including 3% of the light absorber, which is the third sample, has a short-wavelength light transmittance of about 60% to 80%. Accordingly, it may be found that when the content of the light absorber included in the overcoat layer is about 3% or more, the same short wavelength light transmittance is reduced by about 10% or more as compared with the overcoat layer not including any light absorber.

Figure 12:
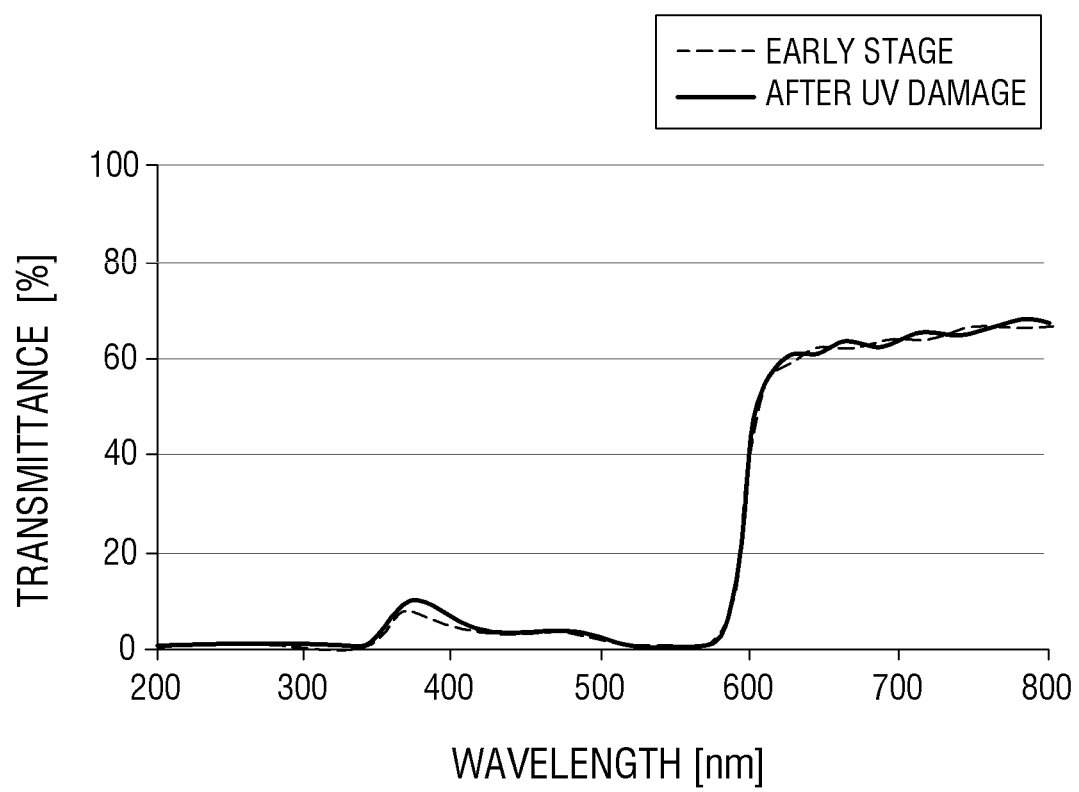
FIGS. 12-17 are graphs illustrating the transmittances of light of red, green, and blue wavelength bands in an overcoat layer not including a light absorber and an overcoat layer including a light absorber.
Figure 13:
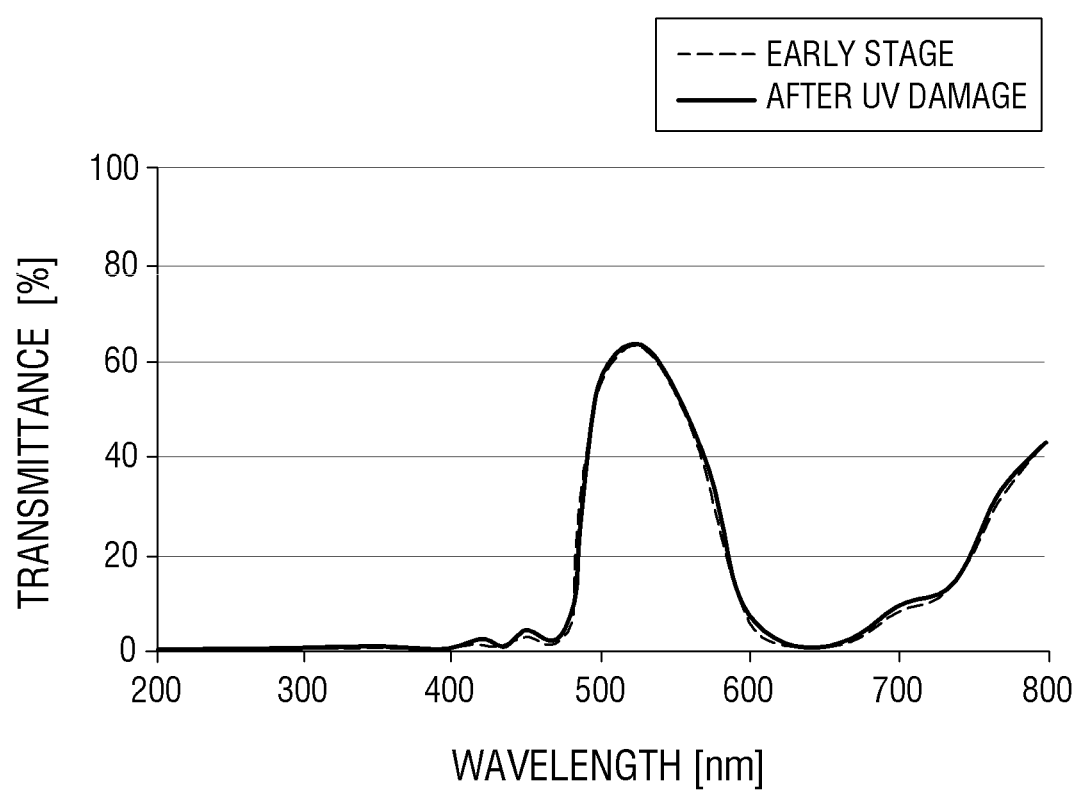
Figure 14:
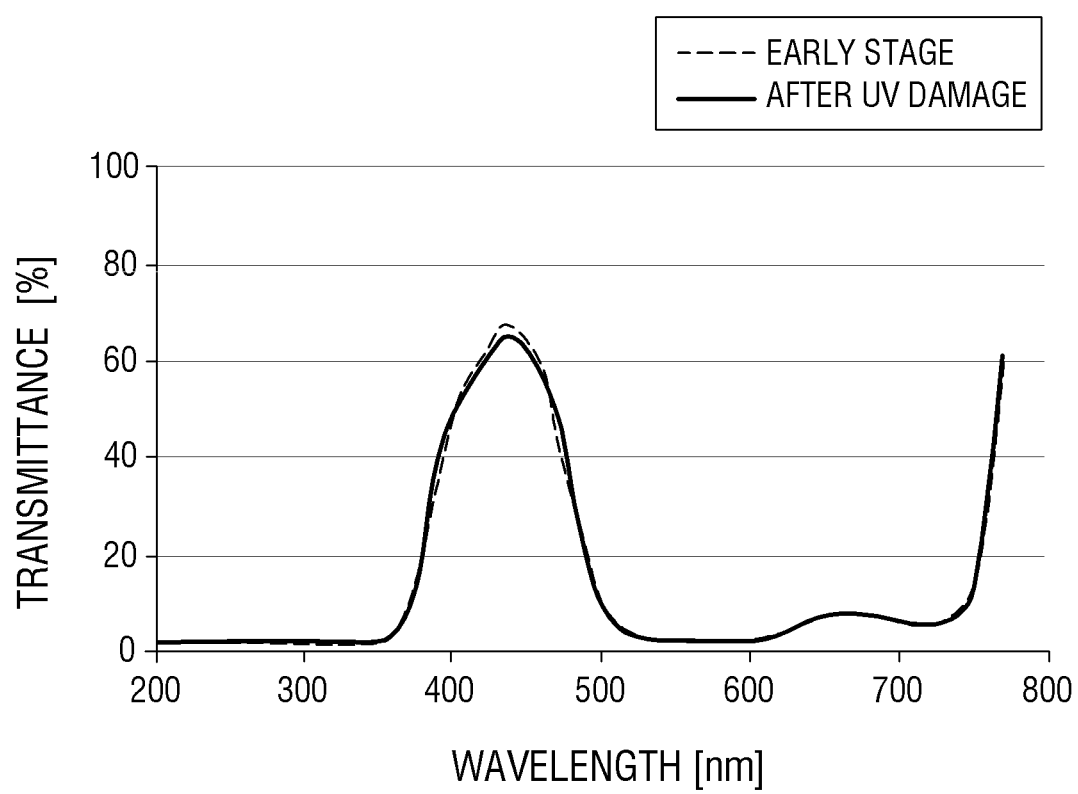

Referring to FIGS. 12 to 14, the blue color filter may substantially transmit light of a wavelength band corresponding to the second color and may absorb light of any wavelength band except for that of the second color, and the red color filter may transmit light of a wavelength band corresponding to the first color. In addition, the red color filter may further transmit light of a wavelength band of about 350 nm to about 380 nm, depending on the constituent material, but the transmission amount thereof may be significantly smaller than that of light of a wavelength band corresponding to the first color. The red color filter may substantially absorb light of wavelengths other than the first color wavelength band and the wavelength band of about 350 nm to about 380 nm. The green color filter may substantially transmit light of the third color and may absorb light of any wavelength band except for that of the third color.

In some embodiments, each of the color filters may have different absorption and transmission patterns when exposed to external light of a short wavelength band. When the red color filter and the blue color filters are exposed to external light of a short wavelength band, the red color filter may be damaged, and as a result, may transmit a larger amount of light of a wavelength of about 350 nm to about 380 nm as compared with the amount of this light before the damage, and the blue color filter may transmit a smaller amount of the wavelength band corresponding to the second color as compared with the amount of this light transmitted before the damage.

Figure 15:
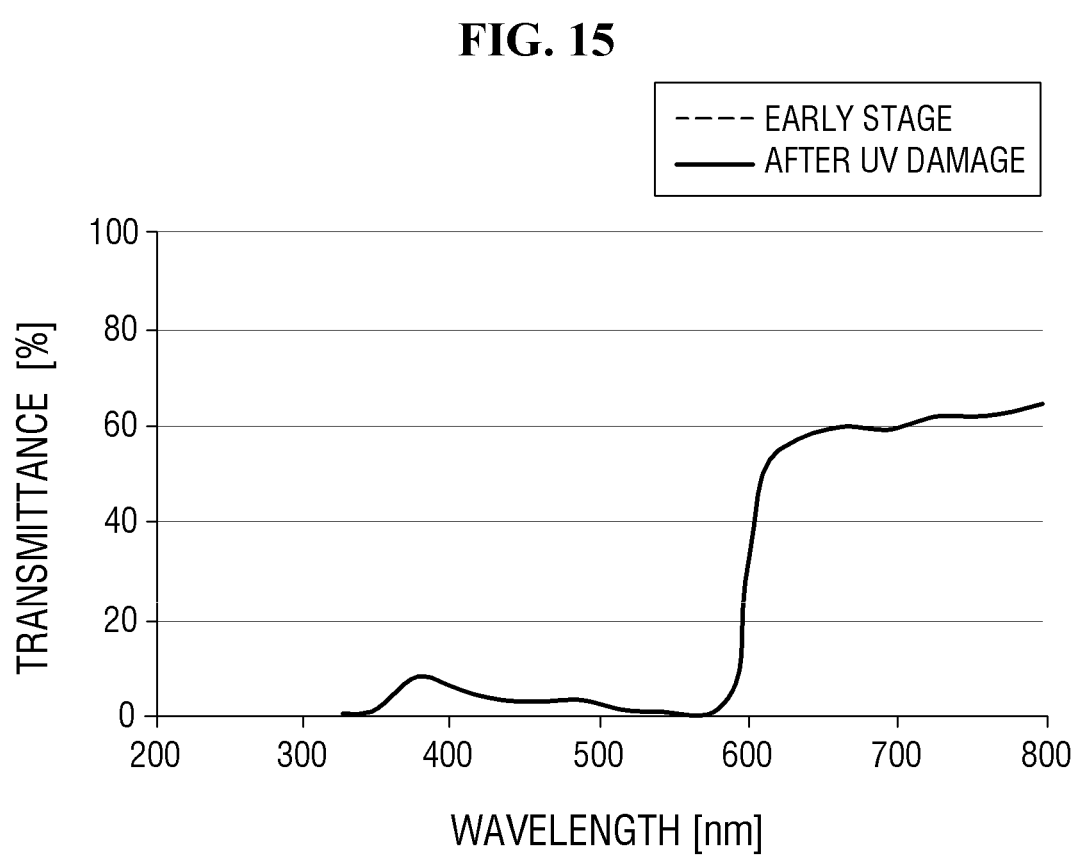
Figure 16:
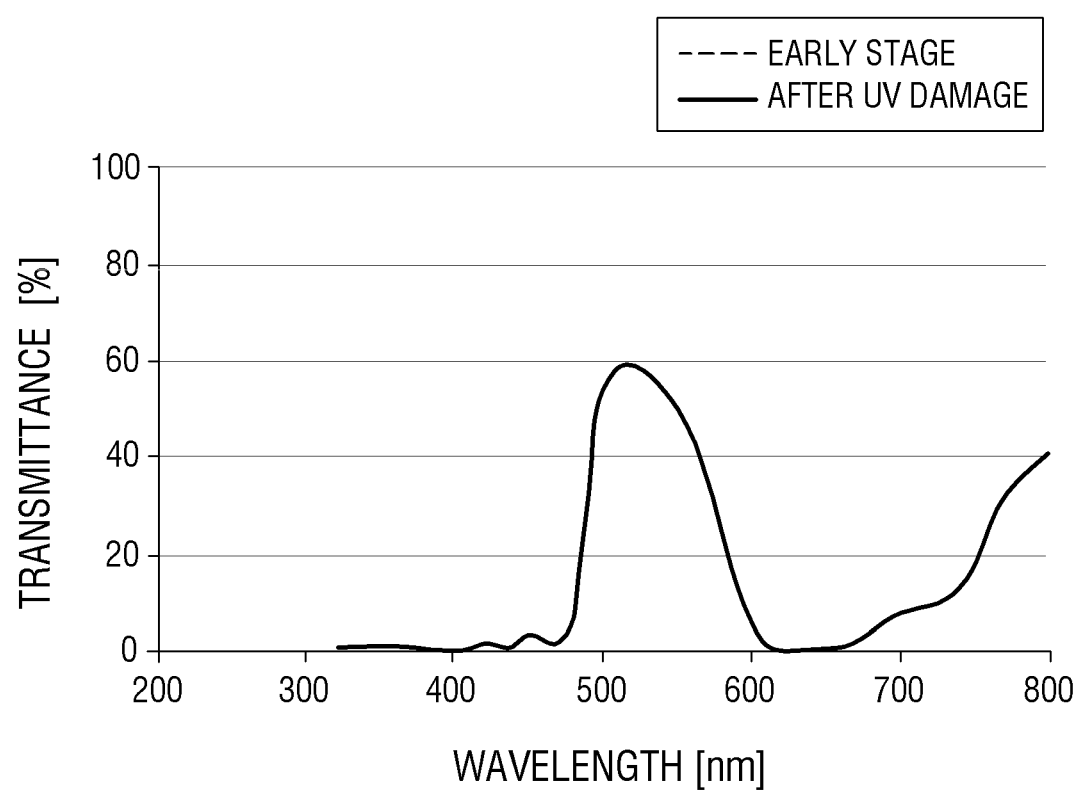
Figure 17:
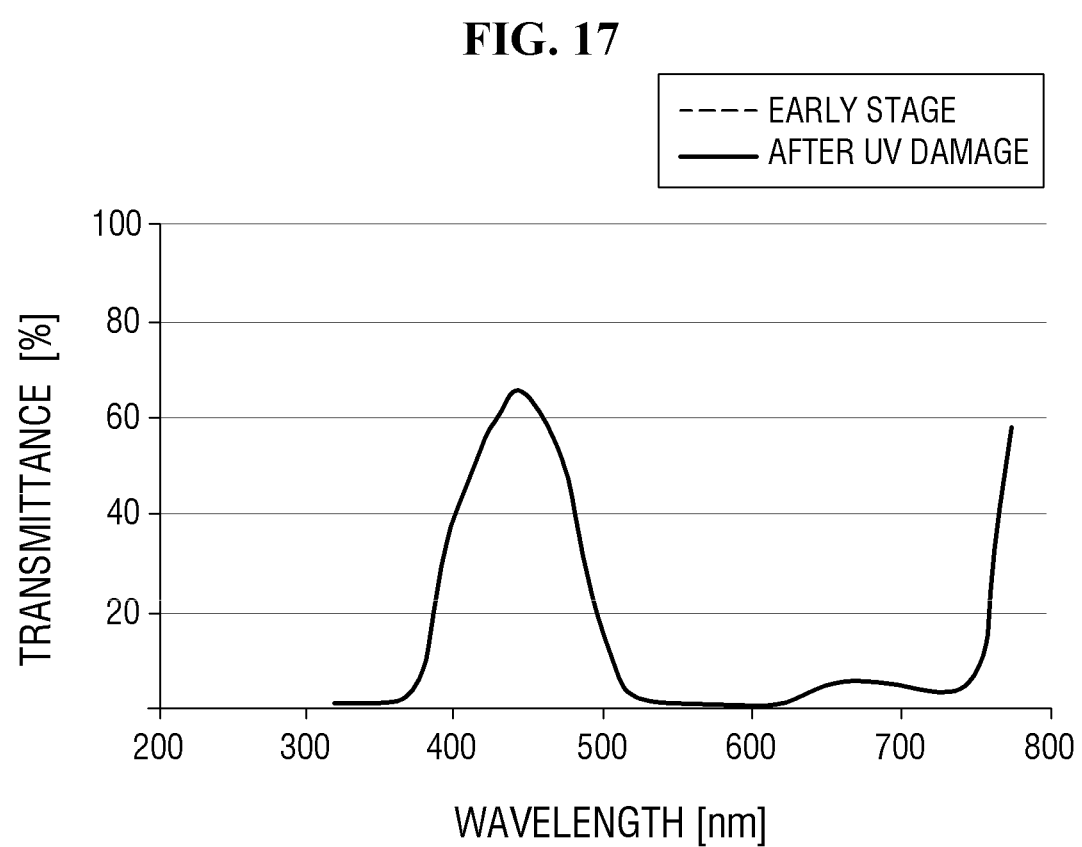

However, referring to FIGS. 15 to 17, it may be found that the aforementioned absorption and transmission patterns caused by the exposure of each color filter to external light of the above short wavelength band hardly change (e.g., even after UV damage).

Hereinafter, other embodiments of the present disclosure will be described.

Figure 18:
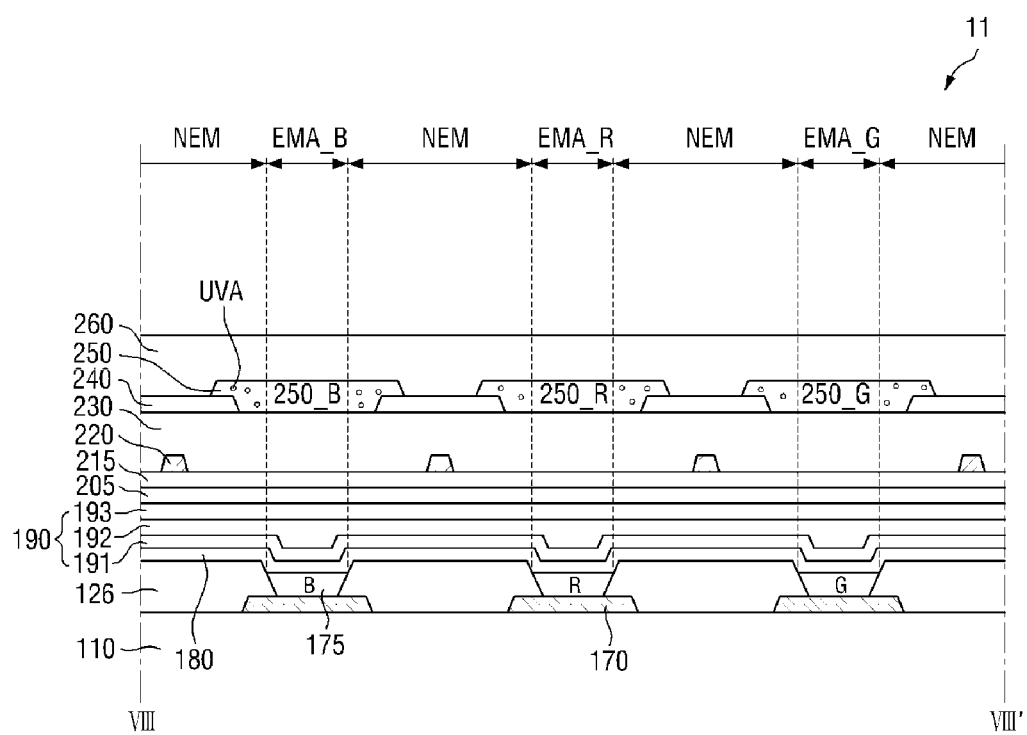
FIG. 18 is a cross-sectional view of a display device according to another embodiment.

FIG. 18 is a cross-sectional view of a display device according to another embodiment.

Referring to FIG. 18, a display device 11 according the present embodiment is different from the display device 10 according to the embodiment of FIG. 8 in that the light absorber UVA represented by Formula 1 is provided in each of the color filter layers 250_R, 250_G, and 250_B.

More specifically, in the display device 11 according the present embodiment, the light absorber UVA represented by Formula 1 may be provided in each of the color filter layers 250_R, 250_G, and 250_B. Because the material of the light absorber UVA and the configuration of the display device have been described above, redundant descriptions thereof will not be provided.

Figure 19:
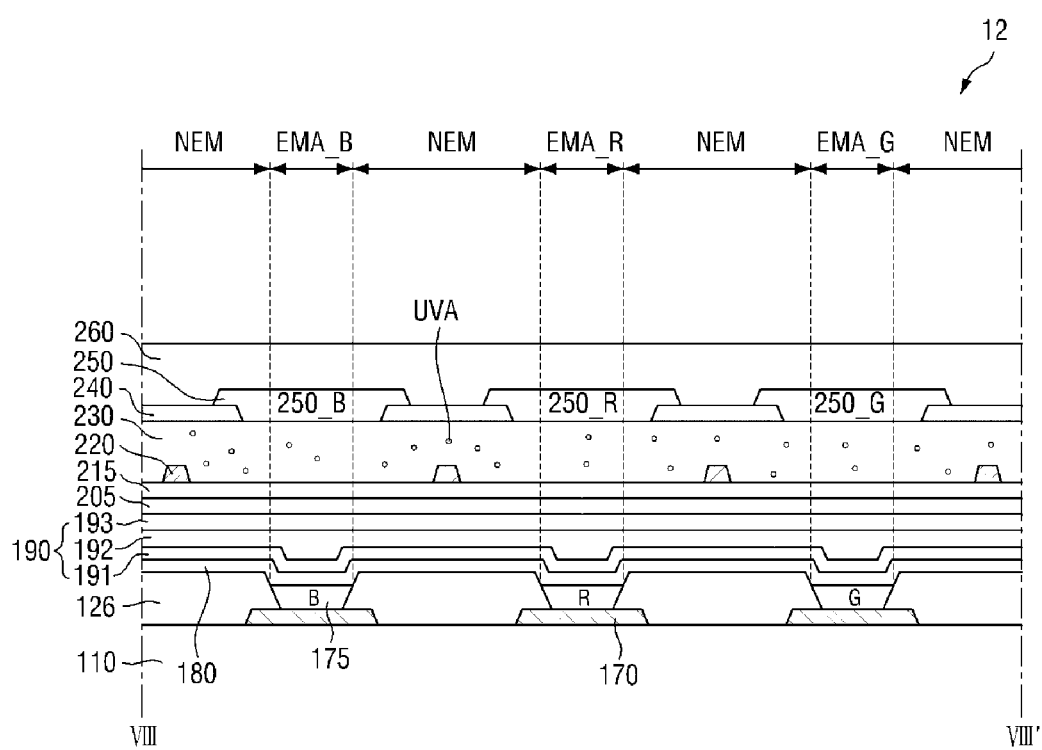
FIG. 19 is a cross-sectional view of a display device according to another embodiment.

FIG. 19 is a cross-sectional view of a display device according to still another embodiment.

Referring to FIG. 19, a display device 12 according the present embodiment is different from the display device 10 according to the embodiment of FIG. 8 in that the light absorber UVA represented by Formula 1 is provided in the second touch insulating layer 230.

More specifically, in the display device 12 according the present embodiment, the light absorber UVA represented by Formula 1 may be provided in the second touch insulating layer 230. Because the material of the light absorber UVA and the configuration of the display device have been described above, redundant descriptions thereof will not be provided.

Figure 20:
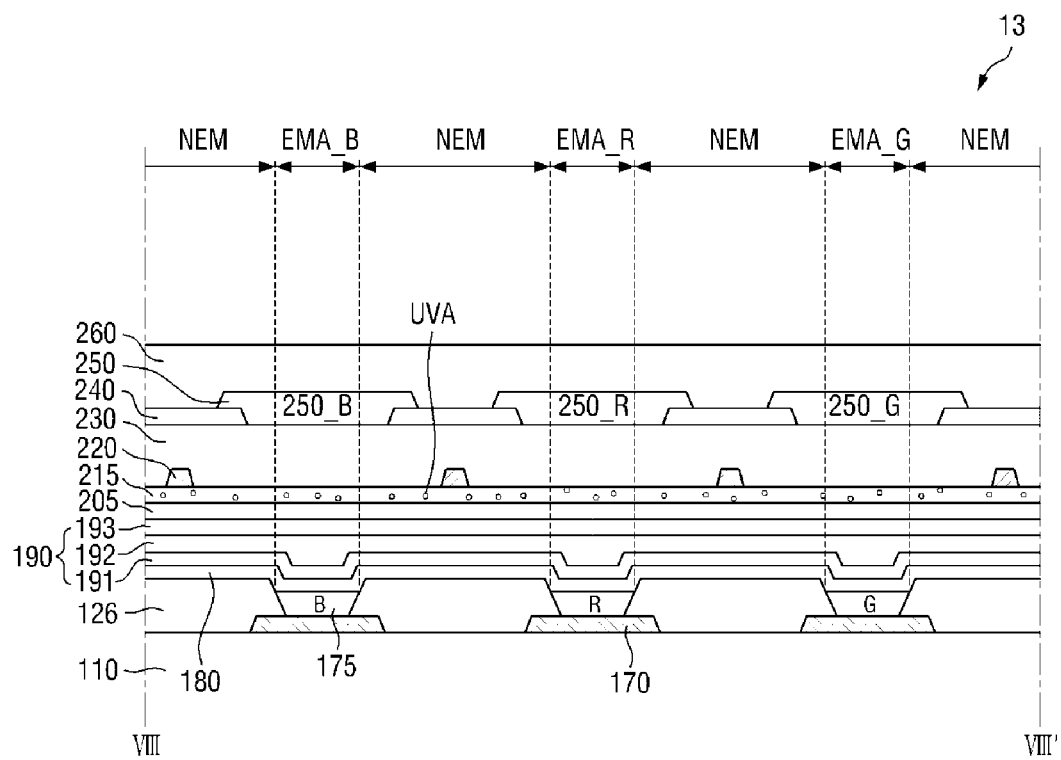
FIG. 20 is a cross-sectional view of a display device according to another embodiment.

FIG. 20 is a cross-sectional view of a display device according to still another embodiment.

Referring to FIG. 20, a display device 13 according the present embodiment is different from the display device 10 according to the embodiment of FIG. 8 in that the light absorber UVA represented by Formula 1 is provided in the first touch insulating layer 215.

More specifically, in the display device 13 according the present embodiment, the light absorber UVA represented by Formula 1 may be provided in the first touch insulating layer 215. Because the material of the light absorber UVA and the configuration of the display device have been described above, redundant descriptions thereof will not be provided.

Figure 21:
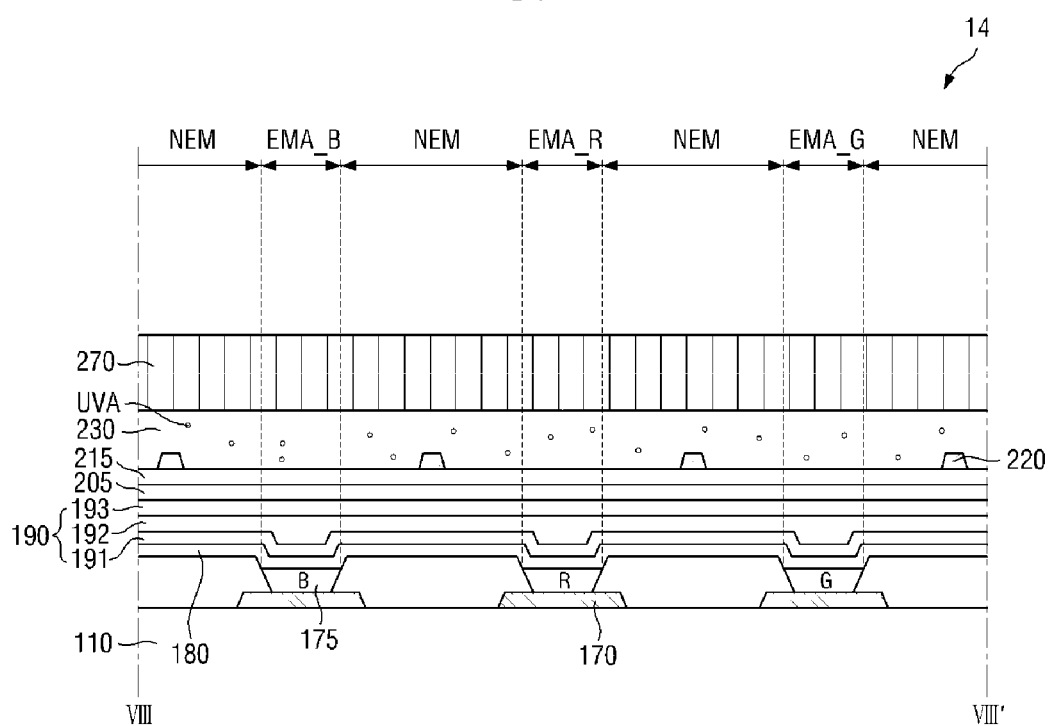
FIG. 21 is a cross-sectional view of a display device according to another embodiment.

FIG. 21 is a cross-sectional view of a display device according to still another embodiment.

Referring to FIG. 21, a display device 14 according the present embodiment is the same as the display device 12 according to the embodiment of FIG. 19 in that the light absorber UVA represented by Formula 1 is provided in the second touch insulating layer 230, but the color filter layer 250 and the overcoat layer 260 on the second touch insulating layer 230 may be omitted, and an optical member 270 may be provided on the second touch insulating layer 230.

More specifically, in the display device 14 according the present embodiment, the light absorber UVA represented by Formula 1 may be provided in the second touch insulating layer 230. In addition, the color filter layer 250 and the overcoat layer 260 on the second touch insulating layer 230 may be omitted, and an optical member 270 may be provided on the second touch insulating layer 230. The optical member 270 may include a polarizing film. The optical member 270 may serve to reduce external light reflection.

The embodiment of FIG. 8, the embodiment of FIG. 18, the embodiment of FIG. 19, and the embodiment of FIG. 20 may be combined with each other within a technical scope of the present disclosure. For example, the light absorber UVA may be provided on two or more of the overcoat layer 260, the color filter layer 250, the second touch insulating layer 230, and the first touch insulating layer 215.

Further, even in the embodiment of FIG. 21, within a technical scope, the light absorber UVA may be provided only in the first touch insulating layer 215 or may be provided in the first touch insulating layer 215 and the second touch insulating layer 230.

According to the display device of the present embodiments, it is possible to prevent or reduce the deterioration of characteristics of a light emitting element.

The effects of the present disclosure are not limited by the foregoing, and other various effects are anticipated herein.

As used herein, the terms "use," "using," and "used" may be considered synonymous with the terms "utilize," "utilizing," and "utilized," respectively.

In addition, the terms "substantially," "about," and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Although the example embodiments of the present disclosure have been disclosed for illustrative purposes, those skilled in the art will appreciate that various modifications, additions and substitutions are possible, without departing from the scope and spirit of the present disclosure as defined by the accompanying claims and their equivalents.

What is claimed is:

1. A display device, comprising:
 a base substrate;
 a light emitting element on the base substrate;
 a thin film encapsulation layer on the light emitting element to encapsulate the light emitting element;
 a touch member on the thin film encapsulation layer;
 a color filter layer on the touch member; and a planarization layer on the color filter layer to cover the color filter layer, wherein the planarization layer comprises a light absorber represented by Formula 1:

X—Ar—Y,   Formula 1 wherein, in Formula 1,

Ar is pyrene, chrysene, or anthracene,

Y is a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or is represented by any one of Structural Formulae:

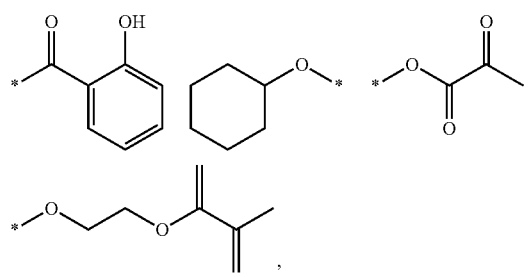

and

X is represented by any one of Formulae 2-1 to 2-3:

Formula 2-1

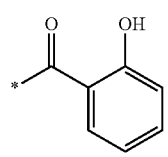

Formula 2-2

Formula 2-3

2. The display device of claim 1,
wherein Formula 1 is represented by any one of Formulae 1-1 to 1-3:

Formula 1-1

Formula 1-2

Formula 1-3

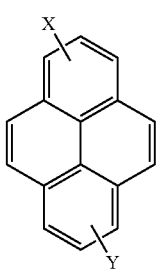

3. The display device of claim 1,
wherein Formula 1 is represented by any one of Formulae 1-4 to 1-6:

Formula 1-4

Formula 1-5

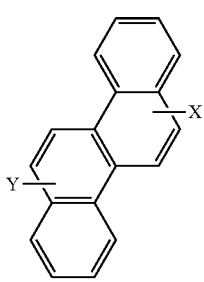

-continued

Formula 1-6

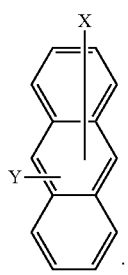

4. The display device of claim 1, wherein Formula 1 is represented by any one of Formulae 1-7 to 1-9:

Formula 1-7

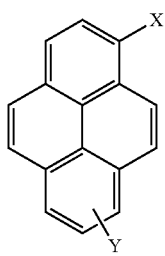

Formula 1-8

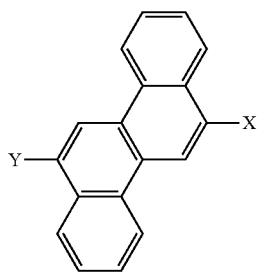

Formula 1-9

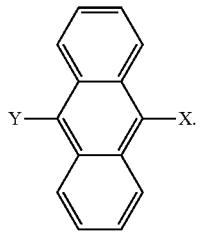

5. The display device of claim 1, wherein X is represented by Formula 2-1, and Y is represented by Formula 3:

Formula 3

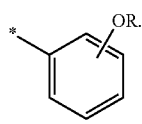

and
wherein R is a substituted or unsubstituted alkyl group having 1 to 5 carbon atoms.

6. The display device of claim 1, wherein the display device has an absorbance of 0.7 or more in a wavelength band of 380 nm to 410 nm.

7. The display device of claim 1, wherein the light absorber represented by Formula 1 is any one selected from compounds represented by Compound Group 1:

2

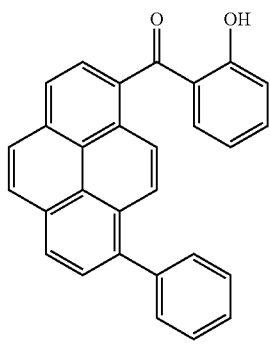

3

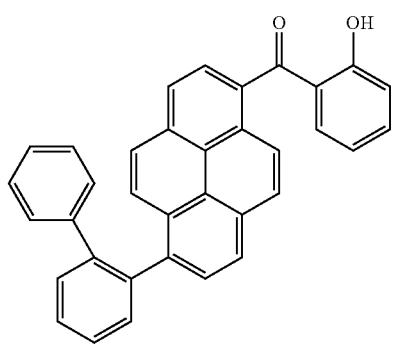

4

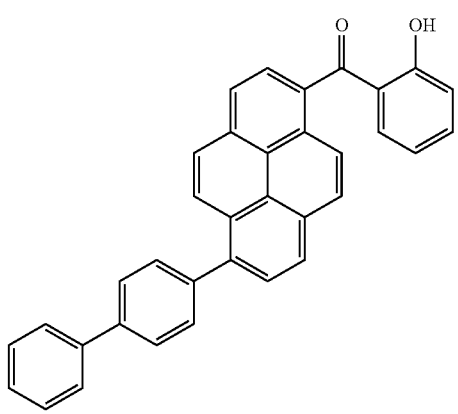

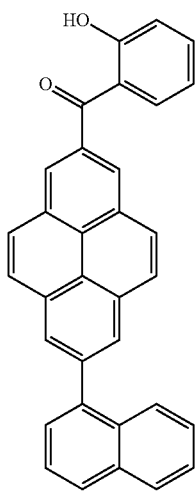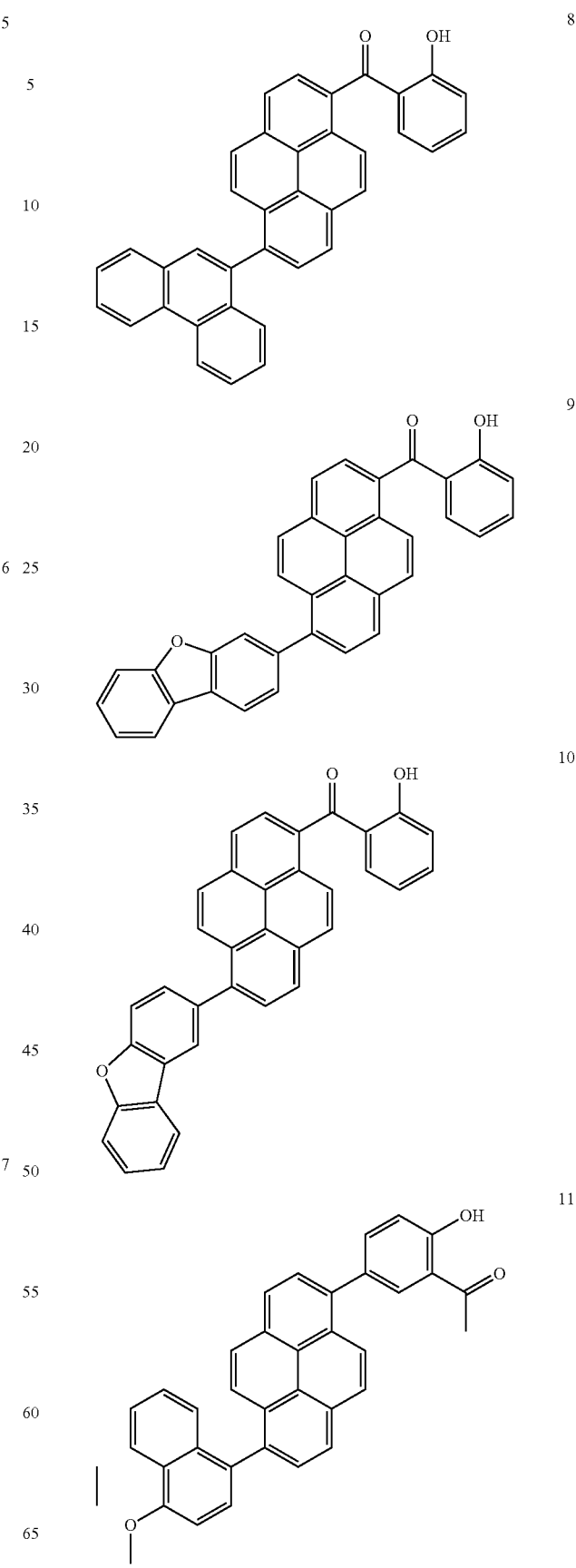

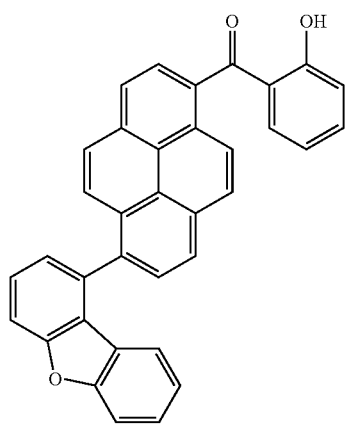
12
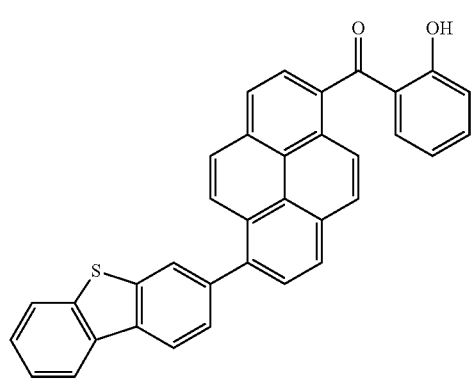
13
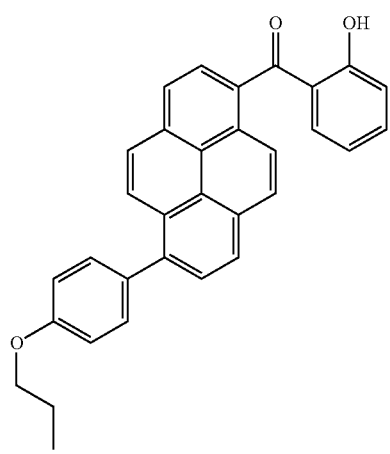
14
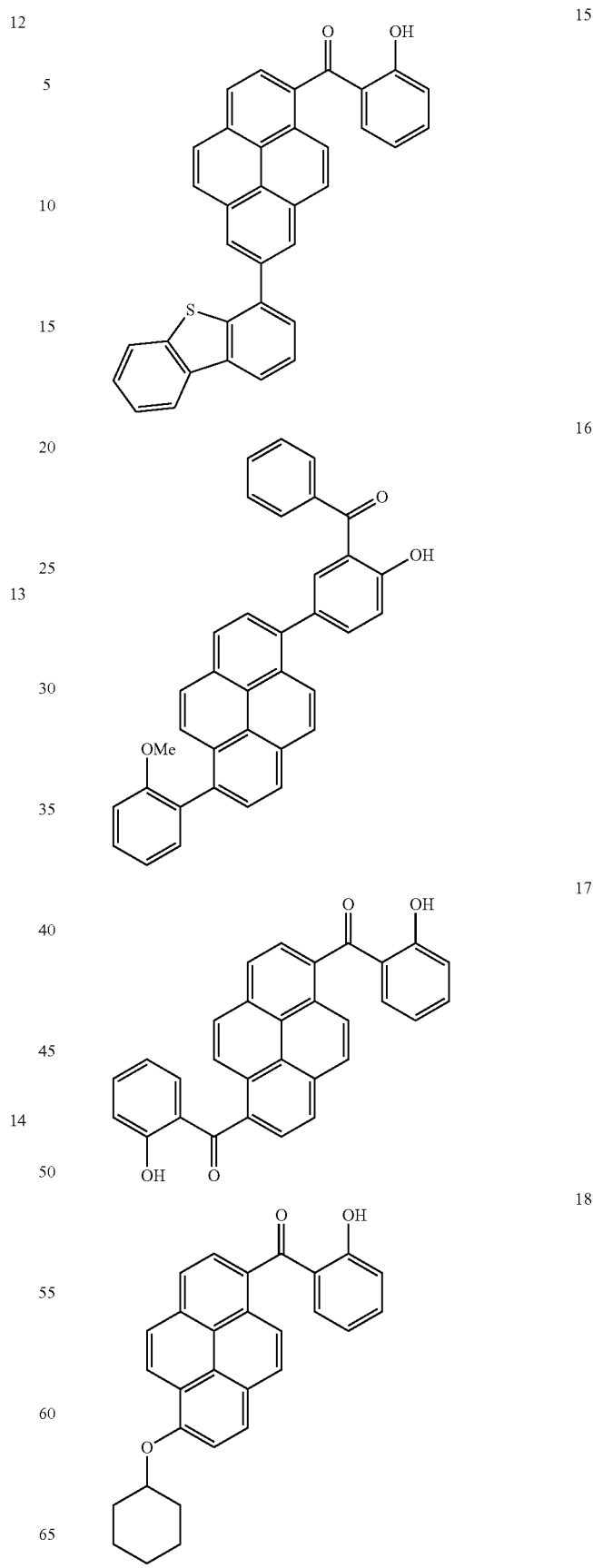

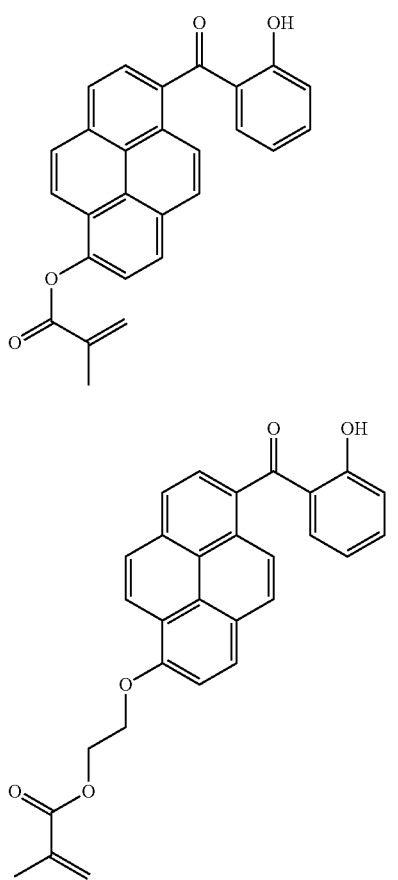
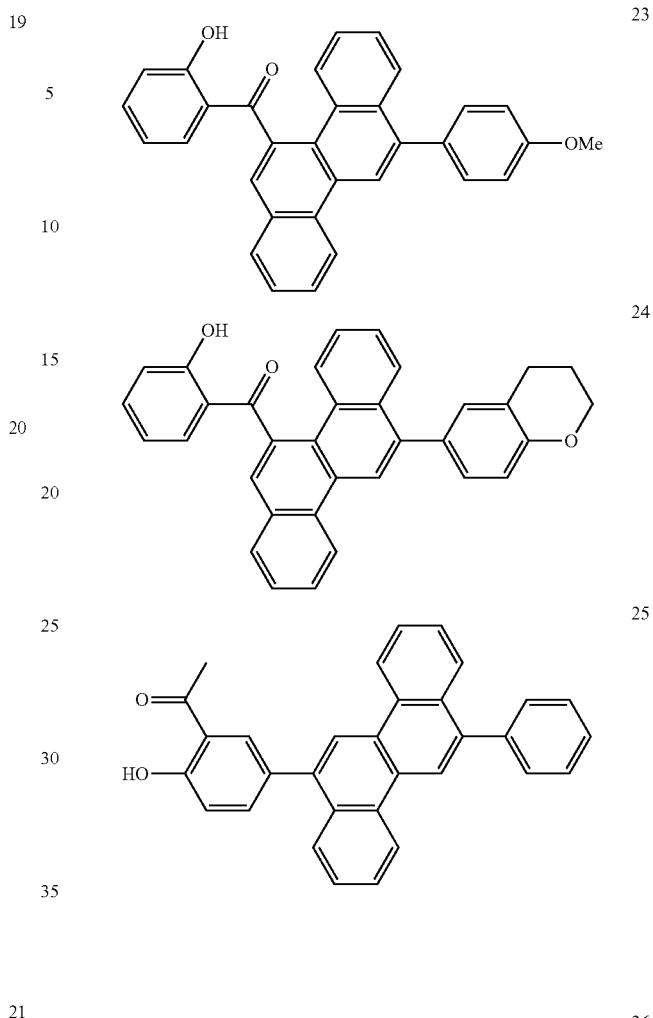
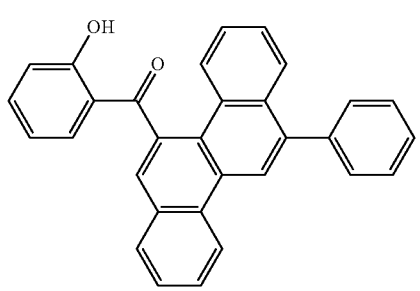
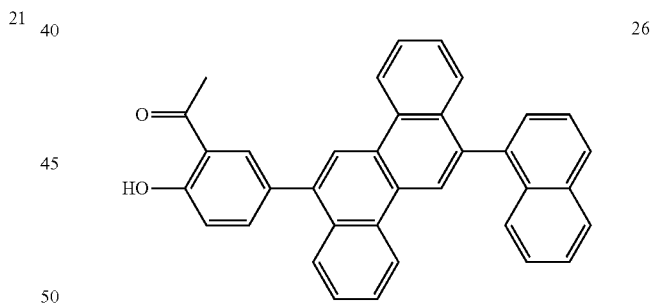
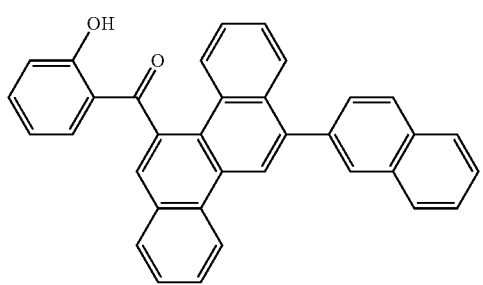
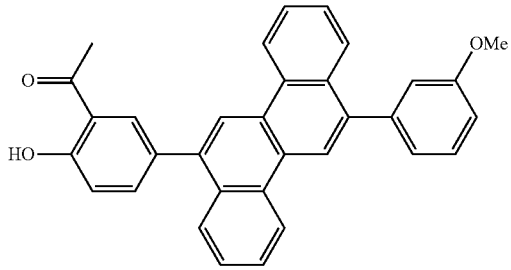

28
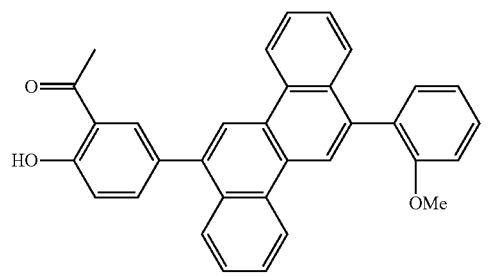
29
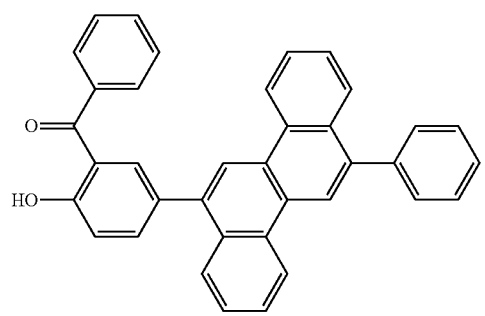
30
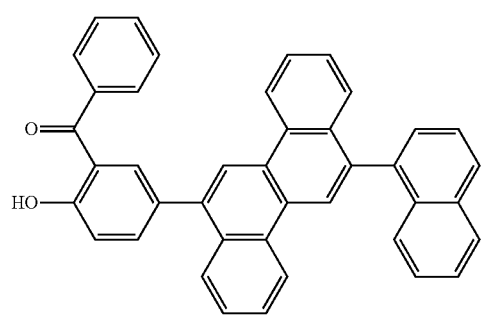
31
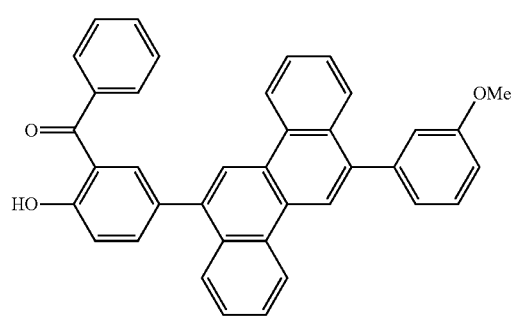
32
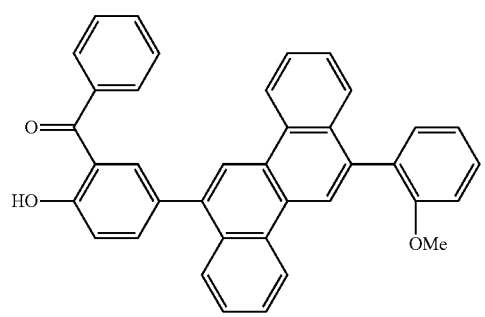
33
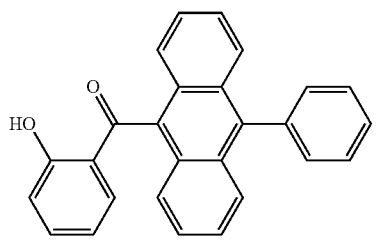
34
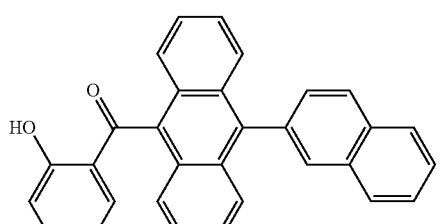
35
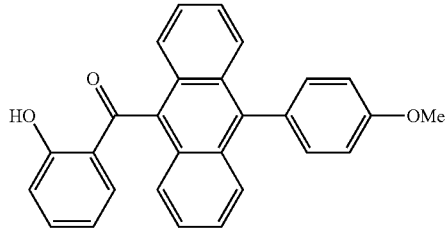
36
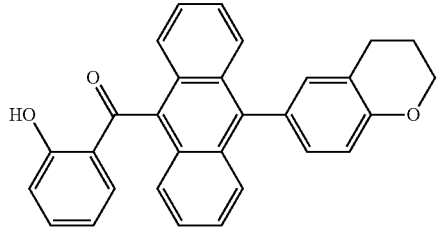
37
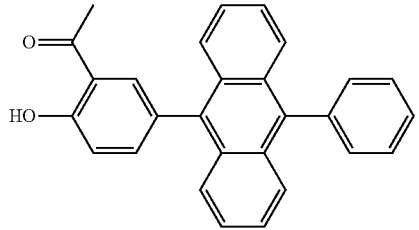
38
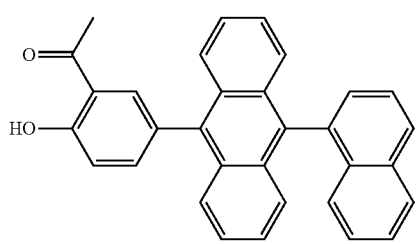

-continued

39
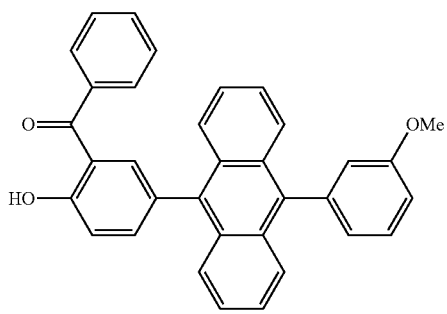

40
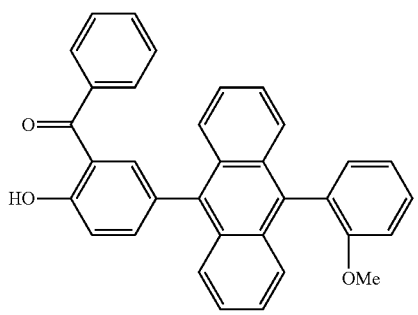

41
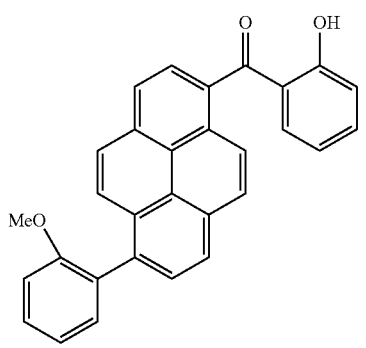

42
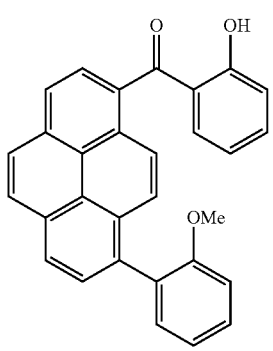

-continued

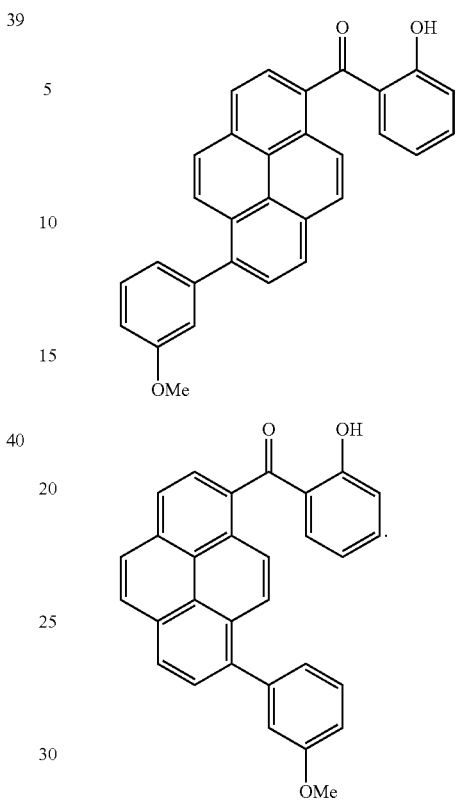

8. The display device of claim 1,
wherein the light absorber is further in the color filter layer.

9. The display device of claim 8,
wherein the color filter layer is provided for each pixel, the color filter layer comprises a plurality of color filters and the plurality of color filters are spaced apart from each other at a boundary between adjacent pixels, and
a light blocking layer is on the touch member at the boundary between adjacent pixels.

10. The display device of claim 1,
wherein the touch member comprises a first touch conductive layer, a first touch insulating layer on the first touch conductive layer, a second touch conductive layer on the first touch insulating layer, and a second touch insulating layer on the second touch conductive layer; and
the light absorber is further in the first touch insulating layer and/or the second touch insulating layer.

11. The display device of claim 10,
wherein the first touch conductive layer is directly on the thin film encapsulation layer.

12. A display device, comprising:
a base substrate;
a light emitting element on the base substrate;
a thin film encapsulation layer on the light emitting element to encapsulate the light emitting element;
a touch member on the thin film encapsulation layer;
a color filter layer on the touch member; and
a planarization layer on the color filter layer to cover the color filter layer,
wherein the planarization layer comprises a light absorber in a content of 3 wt % to 25 wt %.

13. The display device of claim 12, wherein the light absorber is represented by Formula 1:

X—Ar—Y,      Formula 1 wherein, in Formula 1,

Ar is pyrene, chrysene, or anthracene,

Y is a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or is represented by any one of Structural Formulae:

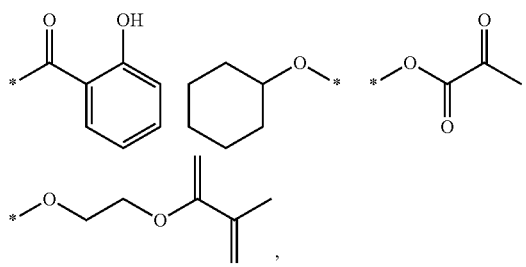

and

X is represented by any one of Formulae 2-1 to 2-3:

Formula 2-1

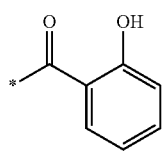

Formula 2-2

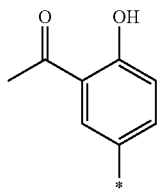

Formula 2-3

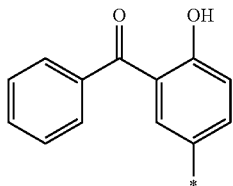

.

14. The display device of claim 12, wherein the light absorber is further in the color filter layer.

15. The display device of claim 14, wherein the color filter layer is provided for each pixel, the color filter layer comprises a plurality of color filters and the plurality of color filters are spaced apart from each other at a boundary between adjacent pixels, and a light blocking layer is on the touch member at the boundary between adjacent pixels.

16. The display device of claim 12, wherein the touch member comprises a first touch conductive layer, a first touch insulating layer on the first touch conductive layer, a second touch conductive layer on the first touch insulating layer, and a second touch insulating layer on the second touch conductive layer; and the light absorber is further in the first touch insulating layer and/or the second touch insulating layer.

17. A display device, comprising:

a base substrate;

a light emitting element on the base substrate;

a thin film encapsulation layer on the light emitting element to encapsulate the light emitting element;

a touch member on the thin film encapsulation layer; and an optical member on the touch member, wherein the touch member comprises a first touch conductive layer, a first touch insulating layer on the first touch conductive layer, a second touch conductive layer on the first touch insulating layer, and a second touch insulating layer on the second touch conductive layer, a light absorber is in the first touch insulating layer and/or the second touch insulating layer, and the light absorber is represented by Formula 1:

X—Ar—Y,      Formula 1 wherein, in Formula 1,

Ar is pyrene, chrysene, or anthracene,

Y is a substituted or unsubstituted phenyl group, a substituted or unsubstituted biphenyl group, a substituted or unsubstituted naphthyl group, a substituted or unsubstituted anthracenyl group, a substituted or unsubstituted phenanthrenyl group, a substituted or unsubstituted dibenzofuranyl group, or a substituted or unsubstituted dibenzothiophenyl group, or is represented by any one of Structural Formulae:

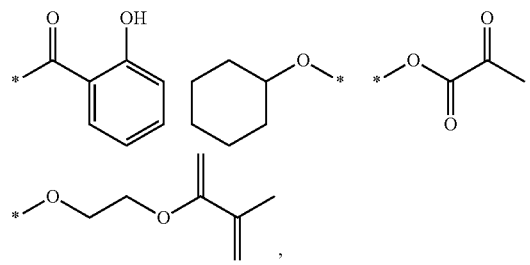

and

X is represented by any one of Formulae 2-1 to 2-3:

Formula 2-1

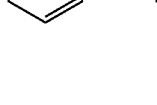

Formula 2-2

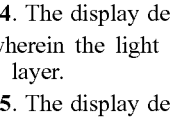

-continued
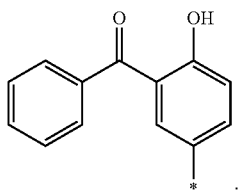
Formulae 2-3
18. The display device of claim 17,
wherein Formula 1 is represented by any one of Formulae 1-1 to 1-3:
Formula 1-1
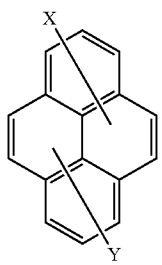
Formula 1-2
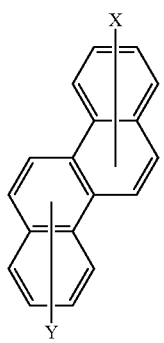
Formula 1-3
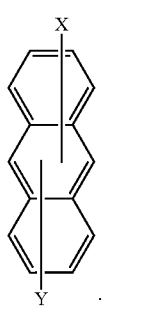
19. The display device of claim 17,
wherein Formula 1 is represented by any one of Formulae 1-4 to 1-6:
Formula 1-4
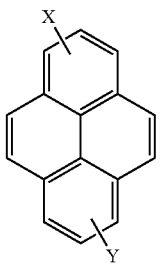
Formula 1-5
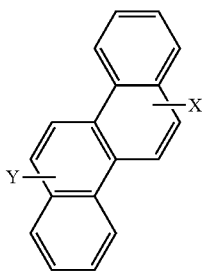
Formula 1-6
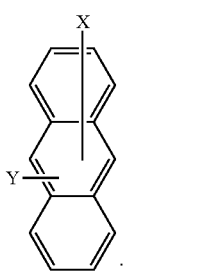
20. The display device of claim 17,
wherein Formula 1 is represented by any one of Formulae 1-7 to 1-9:
Formula 1-7
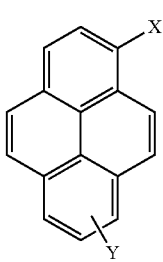
Formula 1-8
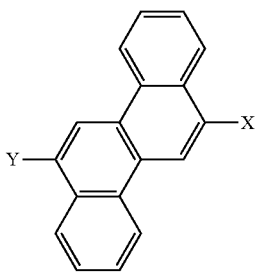

-continued
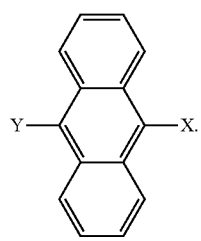
* * * * *